US011241454B2

(12) United States Patent
Pelus et al.

(10) Patent No.: US 11,241,454 B2
(45) Date of Patent: Feb. 8, 2022

(54) MATERIALS AND METHODS TO ENHANCE HEMATOPOIETIC STEM CELLS ENGRAFTMENT PROCEDURES

(71) Applicant: Indiana University Research & Technology Corporation, Indianapolis, IN (US)

(72) Inventors: Louis M. Pelus, Indianapolis, IN (US); Jonathan Hoggatt, Somerville, MA (US); Pratibha Singh, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 15/592,375

(22) Filed: May 11, 2017

(65) Prior Publication Data

US 2017/0304362 A1 Oct. 26, 2017

Related U.S. Application Data

(63) Continuation of application No. 14/638,676, filed on Mar. 4, 2015, now Pat. No. 9,675,641, which is a continuation of application No. 13/128,074, filed as application No. PCT/US2009/063654 on Nov. 6, 2009, now Pat. No. 9,107,909.

(60) Provisional application No. 61/112,018, filed on Nov. 6, 2008.

(51) Int. Cl.
| | |
|---|---|
| *A61K 48/00* | (2006.01) |
| *C12N 5/00* | (2006.01) |
| *C12N 5/071* | (2010.01) |
| *A61K 35/14* | (2015.01) |
| *A61K 31/00* | (2006.01) |
| *C12N 5/0789* | (2010.01) |
| *A61K 31/395* | (2006.01) |
| *A61K 31/405* | (2006.01) |
| *A61K 31/5415* | (2006.01) |
| *A61K 35/28* | (2015.01) |
| *A61K 35/50* | (2015.01) |
| *A61K 35/51* | (2015.01) |
| *A61K 38/19* | (2006.01) |
| *C12N 9/02* | (2006.01) |
| *A61K 31/4035* | (2006.01) |
| *A61K 31/4196* | (2006.01) |
| *C12N 5/16* | (2006.01) |
| *C12N 15/63* | (2006.01) |
| *C12N 15/86* | (2006.01) |
| *A61K 35/12* | (2015.01) |

(52) U.S. Cl.
CPC .............. *A61K 35/14* (2013.01); *A61K 31/00* (2013.01); *A61K 31/395* (2013.01); *A61K 31/405* (2013.01); *A61K 31/4035* (2013.01); *A61K 31/4196* (2013.01); *A61K 31/5415* (2013.01); *A61K 35/28* (2013.01); *A61K 35/50* (2013.01); *A61K 35/51* (2013.01); *A61K 38/193* (2013.01); *C12N 5/0647* (2013.01); *C12N 9/0083* (2013.01); *A61K 2035/124* (2013.01); *C12N 5/16* (2013.01); *C12N 15/63* (2013.01); *C12N 15/86* (2013.01); *C12N 2501/02* (2013.01); *C12Y 114/99001* (2013.01)

(58) Field of Classification Search
CPC .... C12N 15/63; C12N 15/86; C12N 2501/02; C12N 5/0647; A61K 35/28
See application file for complete search history.

(56) References Cited

U.S. PATENT DOCUMENTS

| | | |
|---|---|---|
| 8,029,780 B2 | 10/2011 | Kollet et al. |
| 8,241,903 B2 | 8/2012 | Lapidot et al. |
| 8,367,057 B2 | 2/2013 | Lapidot et al. |
| 2003/0215452 A1 | 11/2003 | Carroll et al. |
| 2005/0163760 A1 | 7/2005 | Cartier-Lacave et al. |
| 2007/0087988 A1 | 4/2007 | Sawasdikosol et al. |
| 2008/0021078 A1 | 1/2008 | Tidmarsh et al. |

(Continued)

FOREIGN PATENT DOCUMENTS

| | | |
|---|---|---|
| JP | 2007099724 | 4/2007 |
| WO | 199211355 | 7/1992 |

(Continued)

OTHER PUBLICATIONS

Zhao et al., 2012, Molecules, vol. 17, p. 6196-6236.
Feher, et al. "Prostaglandin E2 as Stimulator of Haemopoietic Stem Cell Proliferation." Nature, vol. 247, No. 442:550-551 (1974).
North et al., Prostaglandin E2 regulates vertebrate heamatopoietic stem cell homeostasis, 2007, Nature, vol. 447, No. 21, p. 1007-1012.
Taha, Masoumeh F., 2010, Current Stem Cell Research & Therapy, vol. 5, p. 23-36.

(Continued)

*Primary Examiner* — Shin Lin Chen
(74) *Attorney, Agent, or Firm* — Quarles & Brady LLP

(57) ABSTRACT

This disclosure is directed to the methods of enhancing hematopoietic stem cells (HSPC) and progenitor cell (HSPC) engraftment procedure. Treatment in vivo of a HSPC donor with compounds that reduce $PGE_2$ biosynthesis or $PGE_2$ receptor antagonists alone, or in combination with other hematopoietic mobilization agents such as AMD3100 and G-CSF, increases the circulation of available HSPCs. Compounds that reduce the cellular synthesis of $PGE_2$ include non-steroidal anti-inflammatory compounds such as indomethacin. Treatment ex vivo of HSPC with an effective amount of $PGE_2$ or at least one of its derivatives such as 16,16-dimethyl prostaglandin $E_2$ ($dmPGE_2$), promotes HSPC engraftment. Similar methods may also be used to increase viral-mediated gene transduction efficacy into HSPC.

11 Claims, 41 Drawing Sheets

(56) References Cited

U.S. PATENT DOCUMENTS

| | | | |
|---|---|---|---|
| 2008/0207584 A1 | 8/2008 | Habashita et al. | |
| 2008/0261922 A1 | 10/2008 | Carley et al. | |

FOREIGN PATENT DOCUMENTS

| | | | |
|---|---|---|---|
| WO | 199211355 A1 | | 7/1992 |
| WO | WO 95/19793 | * | 7/1995 |
| WO | 199748815 | | 12/1997 |
| WO | 2003029412 | | 4/2003 |
| WO | 2007112084 | | 10/2007 |
| WO | 2007112084 | | 11/2007 |
| WO | 2008072540 | | 6/2008 |
| WO | 2008073748 | | 6/2008 |
| WO | 2008073748 A1 | | 6/2008 |
| WO | WO 2008/073748 A1 | * | 6/2008 |
| WO | 2008070310 | | 12/2008 |
| WO | 2010108028 | | 9/2010 |

OTHER PUBLICATIONS

Li et al., 2009, Transplant Immunology, vol. 21, p. 70-74.
Sprangers et al. 2008, Kidney International, vol. 74, p. 14-21.
Skolnick et al., 2000, Trends in Biotech, vol. 18, p. 34-39.
Tomasinsig et al., 2005, Current Protein and Peptide Science, vol. 6, p. 23-34.
Smallwood et al., 2002, Virology, vol. 304, p. 135-145.
Chattopadhyay et al., 2004, Virus Research, vol. 99, p. 139-145.
Whitehurst et al., 2006, Virology, vol. 347, p. 199-207.
Allegrucci et al., 2006, Human reproduction update, Vol. Advance Access published on Aug. 26, 2006, p. 1-18.
Sato et al., 2003, Developmental Biology, vol. 260, p. 404-413.
Abeyta et al., 2004, human Molecular Genetics, vol. 13, No. 6, p. 601-608.
Kolf et al., 2007, Arthritis Research & Therapy, vol. 9, p. 204, 10 pages.
Alenzi et al., 2011, African Journal of Biotechnology, vol. 10(86), pp. 19929-19940.
McGiff, John, 1981, Ann. Rev. Pharmacal. Toxicol., vol. 21, p. 479-509.
Hoggat et al., Prostaglandin E2 enhances hematopoietic stem cell homing, survival, and proliferation, Blood, vol. 113, No. 22, pp. 5444-5455.
International Search Report, PCT/US2009/063654, dated Jan. 12, 2010, 2 pages.
International Searching Authority, International Preliminary Report on Patentability for PCT/US2009/063654, dated May 2011.
International Searching Authority, Written Opinion for PCT/US2009/063654, dated Jan. 2010.
Allegrucci et al. "Differences between human embryonic stem cell lines." Human reproduction update 13.2 (2007): 103-120.
Sato et al. "Molecular signature of human embryonic stem cells and its comparison with the mouse." Developmental biology 260.2 (2003): 404-413.
Abeyta et al. "Unique gene expression signatures of independently-derived human embryonic stem cell lines." Human molecular genetics 13.6 (2004): 601-608.
Kolf et al. "Mesenchymal stromal cells: biology of adult mesenchymal stem cells: regulation of niche, self-renewal and differentiation." Arthritis research & therapy 9.1 (2007): 1.
Alenzi et al. "Stem cells: Biology and clinical potential." African Journal of Biotechnology 10.86 (2011): 19929-19940.
McGiff, John C. "Prostaglandins, prostacyclin, and thromboxanes." Annual review of pharmacology and toxicology 21.1 (1981): 479-509.
Bank, Arthur. "Hematopoietic stem cell gene therapy: selecting only the best." The Journal of clinical investigation 112.10 (2003): 1478-1480.
Fehér, et al., 1974. Prostaglandin E2 as stimulator of haemopoietic stem cell proliferation. Nature, vol. 247, p. 550-551.
European Search Opinion for EP App. No. 09825528.4, dated Apr. 10, 2013, pp. 1-6.
Zuber Perez, C., Supplementary European Search Report for EP App. No. 09825528.4, dated Apr. 3, 2013, pp. 1-4, Munich.
Goichberg, P. et al., cAMP-induced PKCZ activation increases functional CXCR4 expression on human CD34+ hematopoietic progenitors, Blood, Feb. 1, 2006, pp. 870-879, vol. 107, No. 3.
Gao, L. et al., Changes of T Cell Subsets in the Peripheral Blood of Mice after Mobilization of Hematopoietic Stem Cells by G-CSF and GM-CSF, Acta Academiae Medicinae Xuzhou, Jul. 2007, pp. 1-2, vol. 27, No. 7.
Levesque, J.P. et al., Mobilization of hematopoietic stem cells: state of the art, Current Opinion in Organ Transplantation, Feb. 2008, pp. 53-58, vol. 13, No. 1.
Lord, A.M. et al., Prostaglandin E2 Making More of Your Marrow, Cell Cycle, Dec. 15, 2007, pp. 3054-3057, vol. 6, No. 24.
North, T.E. et al., Prostaglandin E2 regulates vertebrate haematopoietic stem cell homeostasis, Nature, Jun. 21, 2007, pp. 1007-1011, vol. 447, No. 7147.
Hanazono, Yutaka. "Gene Transfer into Human Hematopoietic Stem Cells and Future Perspective." Journal of Clinical and Experimental Medicine, vol. 194, No. 14:1277-1283 (2000) (in Japanese—unable to find English version).
Dupuis et al. "Prostaglandin E2 Stimulates the Growth of Human Blood CD34+ Progenitors." Prostaglandins & other Lipid Mediators, 55: 179-186. (1998).
Horn et al., "Stem cell gene transfer-efficacy and safety in large animal studies," Mol. Therapy, Nature Publishing Group, GB v. 10, No. 3 (2004).
Hall et al., "Decreased homing of retrovirally transduced human bone marrow CD34+ cells in the NOD/SCID mouse model," Experimental Hematology, 34 (2006) 433-42.
Wang et al., "Rapamycin relieves lentiviral vector transduction resistance in human and mouse hematopoietic stem cells," Blood, (2004) 124:913-23.
Orford, K. W., et al. "Deconstructing stem cell self-renewal: genetic insights into cell-cycle regulation." Nature Reviews Genetics 9.2 (2008): 115-128.
Park, F., et al. "Efficient lentiviral transduction of liver requires cell cycling in vivo." Nature genetics 24.1 (2000) 49-52.
Passegue, E., et al. "Global analysis of proliferation and cell cycle gene expression in the regulation of hematopoietic stem and progenitor cell fates." The Journal of experimental medicine 202.11 (2005): 1599-1611.
Roe, T., et al. "Integration of murine leukemia virus DNA depends on mitosis." The EMBO journal 12.5 (1993) 2099-2108.
Tothova, Z., et al. "FoxOs are critical mediators of hematopoietic stem cell resistance to physiologic oxidative stress." Cell 128.2 (2007): 325-339.
Cheng et al., (1997). A GFP reporter system to assess gene transfer and expression in human hematopoietic progenitor cells. Gene therapy, 4(10), 1013-1022.

* cited by examiner

| Weeks Post-transplant | Repopulating Cell Frequency | | |
|---|---|---|---|
| | Vehicle | dmPGE$_2$ | Fold increase |
| 4 | 1:69,466 | 1:16,619 | 4.18 |
| 8 | 1:85,560 | 1:24,613 | 3.48 |
| 12 | 1:85,560 | 1:23,911 | 3.58 |
| 16 | 1:85,560 | 1:23,911 | 3.58 |
| 20 | 1:89,586 | 1:21,753 | 4.12 |

FIG. 1C

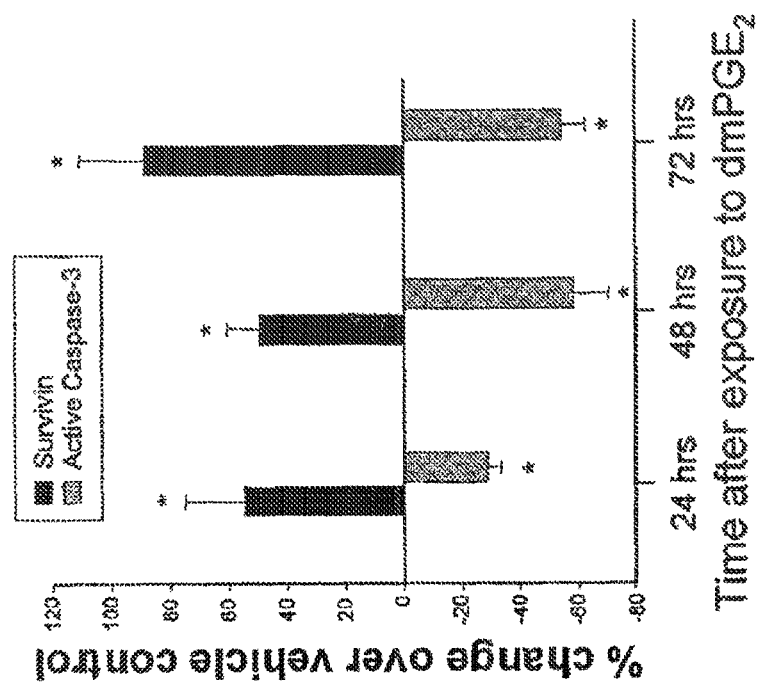

Effects of daily SC administration of 150μg/kg indomethacin or 150 ug/kg baicalein alone (left panel) or with G-CSF (right panel) for 4 days on CFU-GM mobilization. Data are expressed as mean ± SEM CFU-GM mobilized per ml of blood for N = 3 mice each assayed individually.

PGE Increases Cycling of SLAM SKL Cells

Effects of short term in vitro exposure of SLAM SKL cells to dmPGE$_2$ on cell cycle

| In vitro treatment | SLAM SKL Cells | | | |
|---|---|---|---|---|
| | G$_0$ | G$_1$ | S+G$_2$M | % cells in cycle |
| Vehicle | 63.4 ± 2.5 | 2.6 ± 0.7 | 33.8 ± 2.1 | 36.4 ± 2.4 |
| 1 uM dmPGE$_2$ | 54.8 ± 2.2 * | 6.8 ± 1.9 * | 38.4 ± 1.6 * | 45.2 ± 2.2 * |

N=9 mice, each assayed individually

FIG. 8

MATERIALS AND METHODS TO ENHANCE HEMATOPOIETIC STEM CELLS ENGRAFTMENT PROCEDURES

CROSS-REFERENCE TO RELATED APPLICATION

This application is a continuation application of U.S. patent application Ser. No. 14/638,676 filed on Mar. 4, 2015, which was a continuation application of U.S. patent application Ser. No. 13/128,074 filed on Jul. 18, 2011, which was the which is the National Stage of International Application No. PCT/US2009/063654 filed on Nov. 6, 2009, which claims the benefit of U.S. Provisional Patent Application No. 61/112,018 filed on Nov. 6, 2008, the disclosures of which are expressly incorporated herein by reference in its entirety.

STATEMENT OF GOVERNMENTAL RIGHTS

This invention was made with government support under grant numbers HL069669, HL079654, and DK007519 awarded by National Institutes of Health. The U.S. government has certain rights in the invention.

FIELD OF INVENTION

Aspects and embodiment disclosed herein are related to materials and methods for enhancing the engraftment of hematopoietic stem and progenitor cells.

BACKGROUND

Hematopoietic stem and progenitor cell (HSPC) transplantation is a proven therapy for the treatment of certain malignant and nonmalignant hematologic diseases and metabolic disorders. Sources of HSPC for transplantation include bone marrow, mobilized peripheral blood, and umbilical cord blood (UCB) (Goldman and Horowitz, 2002; Fruehauf and Seggawiss, 2003: Broxmeyer, et al., 2006). Physicians routinely perform transplants of bone marrow, mobilized peripheral blood stem cells and umbilical cord blood. These procedures require that sufficient numbers of hematopoietic stem and progenitor cells be harvested from healthy normal donors, or from patients before they develop a given condition or while they are in remission. The harvested materials are subsequently administered to patients whose hematopoietic system and presumably its diseased or malformed tissues and cells have been eradicated. After transplantation, the transplanted stem cells travel to or "home" to the appropriate bone marrow microenvironment niches, lodge within such niches, proliferate and produce new stem cells, a process called self-renewal (Porecha, et al., 2006; Broxmeyer, 2006; Hall et al., 2006). The cells also differentiate into lineage restricted progenitor cells and mature cells, thus restoring the blood forming hematopoietic system necessary for the health of the recipient. Progenitor cells are usually present in the transplanted materials and may be required in these grafts in order to produce mature cells. However, since progenitor cells are not stem cells and cannot self-renew, they participate in transplant therapy for only a limited period of time.

Because the transplant procedure stresses the transplanted material, a successful transplant requires that sufficient cells be transplanted to account for cells killed or damaged during the procedure. This presents a large problem for the transplant of umbilical cord blood grafts as these grafts include very limited numbers of stem cells. For this reason, cord blood grafts usually cannot be used to successfully transplant adults. Similarly 10-25% of patients and normal donors fail to mobilize sufficient cells for use in transplant procedures. In some patient populations, particularly those treated with some chemotherapeutic agents, failure to mobilize is seen in upward of 50% of patients. In general, the more cells that can be transplanted the greater the likelihood that the transplant will be successful, for example, current best practices recommend that peripheral blood stem cell transplantation procedures typically require minimum administration of approximately 2 million $CD34^+$ cells per kilogram of recipient patient body weight, the more CD34+ cells that can be acquired and subsequently transplanted, the better the patient outcome (Pulsipher, 2009).

Inadequate stem cell number, inability to migrate/home to appropriate marrow niches, or poor engrafting efficiency and self-renewal of hematopoietic stem and progenitor cells can adversely affect transplant outcome, measured by the multi-step process of repopulation. Numerous approaches have been tried to try and expand the number of human hematopoietic stem and progenitor cells within isolated grafts in ex vivo settings with limited success. Strategies to improve HSPC transplantation efficacy is needed to overcome the challenge faced by the medical profession. Some aspects and embodiments of the invention disclosed herein address this need.

SUMMARY

Some aspects of the disclosure are directed to the enhancement of hematopoietic stem and progenitor cells harvesting and/or engraftment, some of these aspects include, but are not limited to, ex vivo survival, self-renewal and homing to appropriate marrow niches to increase the success rate for hematopoietic stem and progenitor cell therapy.

Some aspects of the disclosure include methods directed towards increasing the number of hematopoietic stem and progenitor cells with long-term repopulation capabilities harvested from a donor. Some of these methods comprise the steps of: identifying a compound that inhibits the biosynthesis of a prostaglandin, such as prostaglandin E, or a compound that antagonizes at least one prostaglandin receptor involved in the prostaglandin response; and providing a pharmaceutically effective amount of the compound(s) to the donor prior to harvesting hematopoietic stem and progenitor cells from the donor's peripheral blood or bone marrow. In one embodiment, the application of prostaglandin E biosynthesis inhibitor and/or prostaglandin E's receptor antagonist is coupled with one or more clinically approved hematopoietic stem and progenitor cell mobilization agents, for example, Granulocyte-Colony Stimulating Factor (G-CSF), to increase the number of hematopoietic stem and progenitor cells that can be collected by apheresis for hematopoietic graft transplantation. In one embodiment, the compound is selected from cylooxygenase inhibitors, including for example, indomethacin (2-{1-[(4-chlorophenyl)carbonyl]-5-methoxy-2-methyl-1H-indol-3-yl}acetic acid) or a pharmaceutically acceptable salt thereof. In still other embodiments the cyclooxygnease inhibitor is chosen from the group consisting of, aspirin, ibuprofen, Celecoxib, Rofecoxib, Meloxicam, Etoricoxib, Valdecoxib, Naproxen, Diclofenac, Licofelone, Etodolac, Ketorolac or pharmaceutically acceptable salts thereof. In some embodiments the cyclooxygenase inhibitor acts on both COX-1 and COX-2 often times with a preference for COX-2. Still another compound that can be used in some embodiments is Meloxicam.

Other aspects of the disclosure include methods for enhancing a harvested hematopoietic stem and/or progenitor cells graft's long term repopulation capability in a recipient. This may be of particular utility in situations in which the recipient has a compromised hematopoietic system. The method comprises the steps of: a) harvesting a graft from a donor, wherein the donor has been treated with an effective amount of compound to inhibit the biosynthesis of prostaglandin $E_2$ and/or antagonist of prostaglandin $E_2$ receptor; b) contacting the graft with an effective amount of prostaglandin $E_2$ or one or more of its derivatives ex vivo; and c) applying the treated graft to the recipient. In one embodiment, the method further comprises the step of supplying an effective amount of prostaglandin $E_2$ or one of its derivatives or any molecule that has $PGE_2$ activity to a transplant recipient in order to enhance the homing of the graft materials to their appropriate therapeutic niches.

Other aspects of the disclosure include methods for enhancing viral transduction efficacy in stem cells. Some of these methods may include the steps of: providing a viral vector that contains at least one gene of interest for transduction; providing at least one stem cell that has been ex vivo treated by an effective amount of prostaglandin $E_2$ or its derivatives, and transfecting the viral vector to the $PGE_2$ or its derivative treated stem cell.

Some embodiments include methods of enhancing the mobilization of hematopoietic stem and/or progenitor cells, comprising the steps of: identifying a source of hematopoietic stem and/or progenitor cells; providing a compound that reduces the biosynthesis and/or activity of $PGE_2$; and contacting the source of hematopoietic stem and/or progenitor cells with an effective amount of said compound that reduces the cells $PGE_2$ biosynthesis and/or activity. In some embodiments the compound that reduces $PGE_2$ activity is a nonsteroidal antiinflammatory compound, wherein the non-steroidal anti-inflammatory compound acts on both cyclooxygenase-1 and cyclooxygenase-2. In some embodiments the nonsteroidal anti-inflammatory compound acts primarily on cyclooxygenase-2. In some embodiments the non-steroidal anti-inflammatory compound is selected from the group consisting of: aspirin, celecoxib, rofecoxib, etoricoxib, valdecoxib, ibuprofen, naproxen, diclofenac, etodolac, ketrolac and licofelone. In still other embodiments the non-steroidal anti-inflammatory compound is indomethacin and in yet other embodiments the non-steroidal anti-inflammatory compound is meloxicam.

In some embodiments the non-steroidal anti-inflammatory compound is administered to a patient for a period of time overlapping with co-treatment with at least one additional compound that enhances the mobilization of hematopoietic stem and progenitor cells. In some embodiments the compound that enhances the consisting of: G-CSF and plerixafor. In some embodiments the non-steroidal anti-inflammatory compound is administered to a patient for at least 3 days.

Still other embodiments include methods of enhancing the mobilization of hematopoietic stem and/or progenitor cells from a donor, comprising the steps of: providing a compound that is an antagonist of at least one $PGE_2$ receptor; and administering an effective amount of said compound to a hematopoietic stem or progenitor cell donor prior to harvesting hematopoietic stem or progenitor cells from the donor. In some embodiments the antagonist of at least one $PGE_2$ receptor is selected from the groups consisting of: N-[[4'-[[3-butyl-1,5-dihydro-5-oxo-1-[2-(trifluoromethyl)phenyl]-4H-1,2)4-triazol-4-yl]methyl][1,r-biphenyl]-2-yl]sulfonyl]-3-methyl-2-thiophenecarboxamide (L-161, 982) and 4-(4,9-diethoxy-1,3-dihydro-1-oxo-2H-benz[fJi-soindol-2-yl)-N-(phenylsulfonyl)-benzeneacetamide (GW627368X).

Yet other embodiments include engrafting hematopoietic stem and or progenitor cells into recipient, comprising the steps of: harvesting a group of cells that includes hematopoietic stem and progenitor cells from a source that has been treated with at least one compound that reduces $PGE_2$ biosynthesis and/or activity in the source; contacting the set hematopoietic stem cells with a compound with $PGE_2$ activity ex vivo; and transplanting said hematopoietic stem and progenitor cells contacted with said compound that increases $PGE_2$ activity ex vivo, into a recipient. In some embodiments the hematopoietic stem cells are drawn from a bone marrow donor. While in still other embodiments the hematopoietic stem cells are harvested from a sample of blood drawn from a blood donor. And still other embodiment the cells are drawn from an umbilical cord or a placenta.

Some embodiments include method of increasing hematopoietic stem and/or progenitor cell engraftment rates, comprising the steps of providing a compound with $PGE_2$ activity; and contacting the compound with $PEG_2$ activity with a population of hematopoietic stem and/or progenitor cells ex vivo. In some embodiments the compound with $PGE_2$ activity, is selected from the group consisting of any E series prostaglandin or any derivative of an E series prostaglandin, such as $PGE_1$, $PGE_2$, $PGE_3$ or the dimethyl derivatives of $PGE_1$, $PGE_2$, $PGE_3$, including, for example, dimethyl 16, 16-dimethyl $PGE_2$. In some embodiments the compound having $PGE_2$ activity is contacted with the hematopoietic stem and/or progenitor cell population for at least 1 hr. Some embodiments include the steps of washing the hematopoietic stem and/or progenitor cells that were in contact with the compound having $PGE_2$ activity, at least once with a buffer that is substantially free of $PGE_2$ activity. While still other embodiments further include the step of: introducing the hematopoietic stem and/or progenitor cells that were in contact with the compound having $PGE_2$ activity into a patient.

These and other features, aspects and advantages of the present invention may be better understood with reference to the following non limiting drawings, description and claims.

FIG. ID. Representative FACS plots of multi-lineage reconstitution (myeloid, B and T-lymphoid, upper left panel). Plot of counts per CD3 (upper row right panel). Middle row, bar graphs percent of Total WBC measured at 32 weeks in primary recipients (left panel) and 12 weeks in secondary recipients (right panel).

Plot of percent chimerism measured at 20 weeks in primary recipients and 12 weeks in secondary recipients (bottom panel).

Figure 2A:
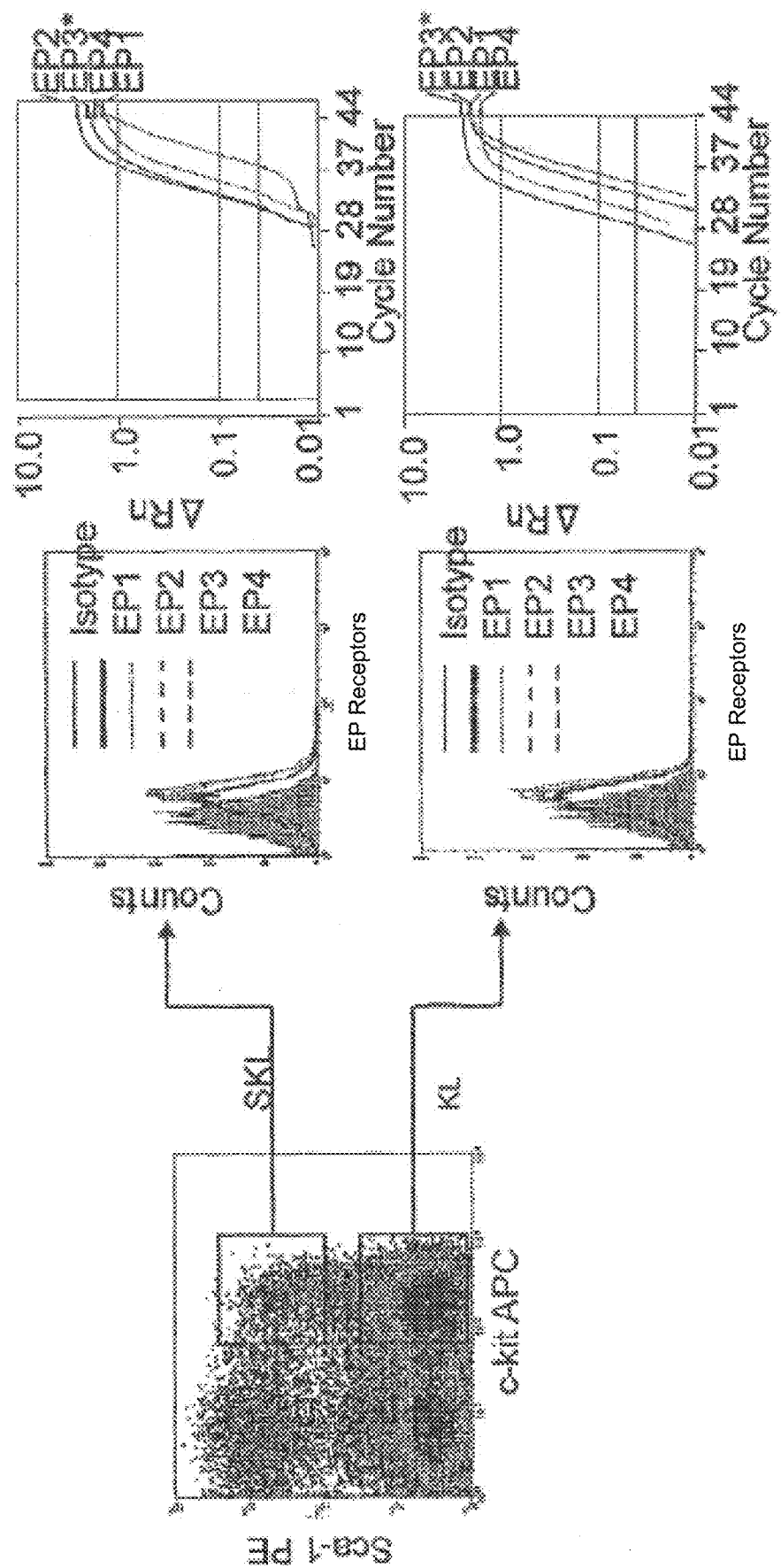

FIG. 2A. Representative FACS gating of MACS microbead depleted Lin$^{neg}$ marrow showing c-kit$^+$ and Sca-1$^+$ gating of Lin$^{neg}$ gated cells (left side panel). Count plotted for different EP receptors (middle panels) and change in mRNA versus cycle number potted for different receptors (right panels).

Figure 2B:
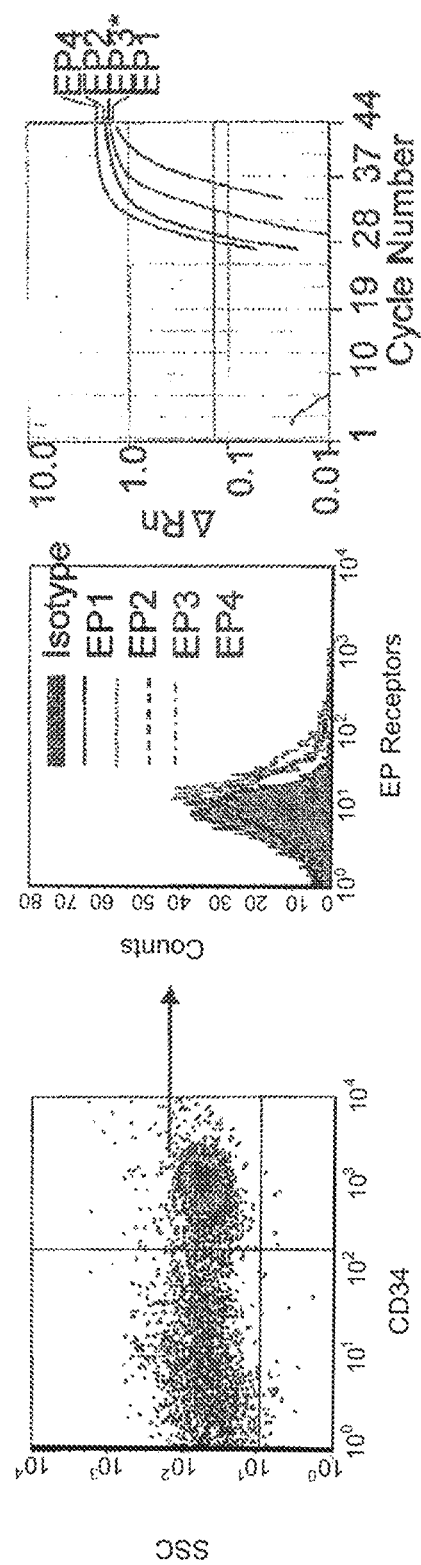

FIG. 2B. Representative FACS SSC versus CD34 (left panel); Counts plotted for different EP receptors (middle panel) and Change in mRNA plotted versus Cycle Number for different receptors (right panel).

Figure 3A:
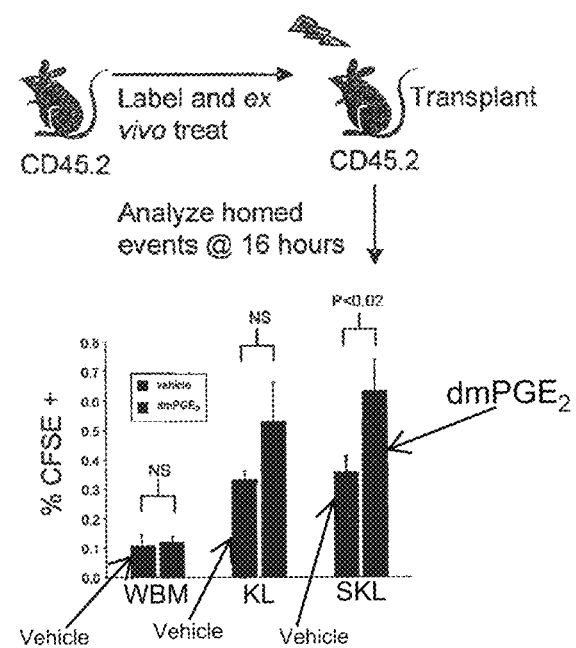

FIG. 3A. Outline of experiment (top); % CFSE+ plotted for different treatments (bottom panel).

Figure 3B:
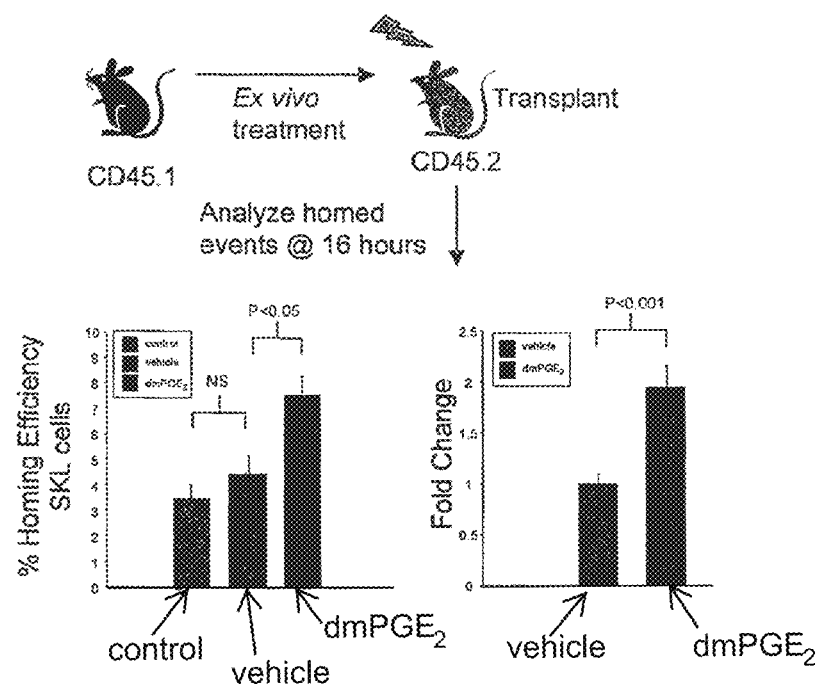

FIG. 3B. Diagram illustrating experimental protocol; percent homing efficiency (lower left panel) and Fold Change (lower right panel) measured after exposure to 16,16-dimethyl prostaglandin E$_2$ (dmPGE$_2$) and various controls.

Figure 3C:
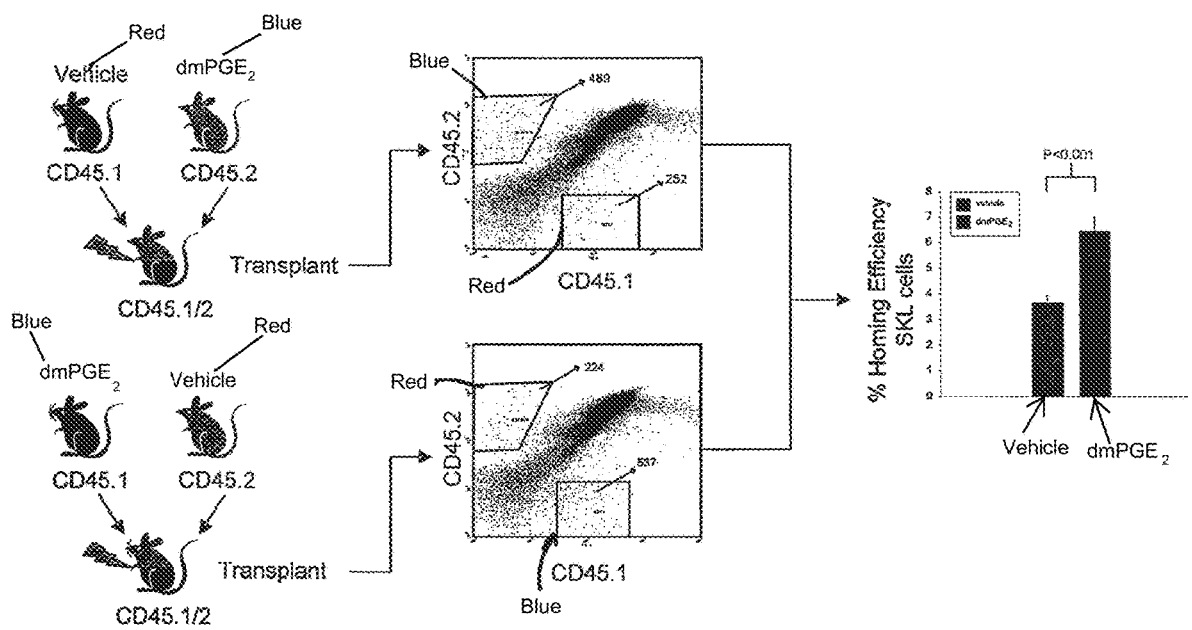

FIG. 3C. Outlines of experiments (left panels); FACS plots of CD45.2 versus CD45.1 for different treatments (middle panels); percent homing efficiency plotted for different treatments (right panels).

Figure 4A:
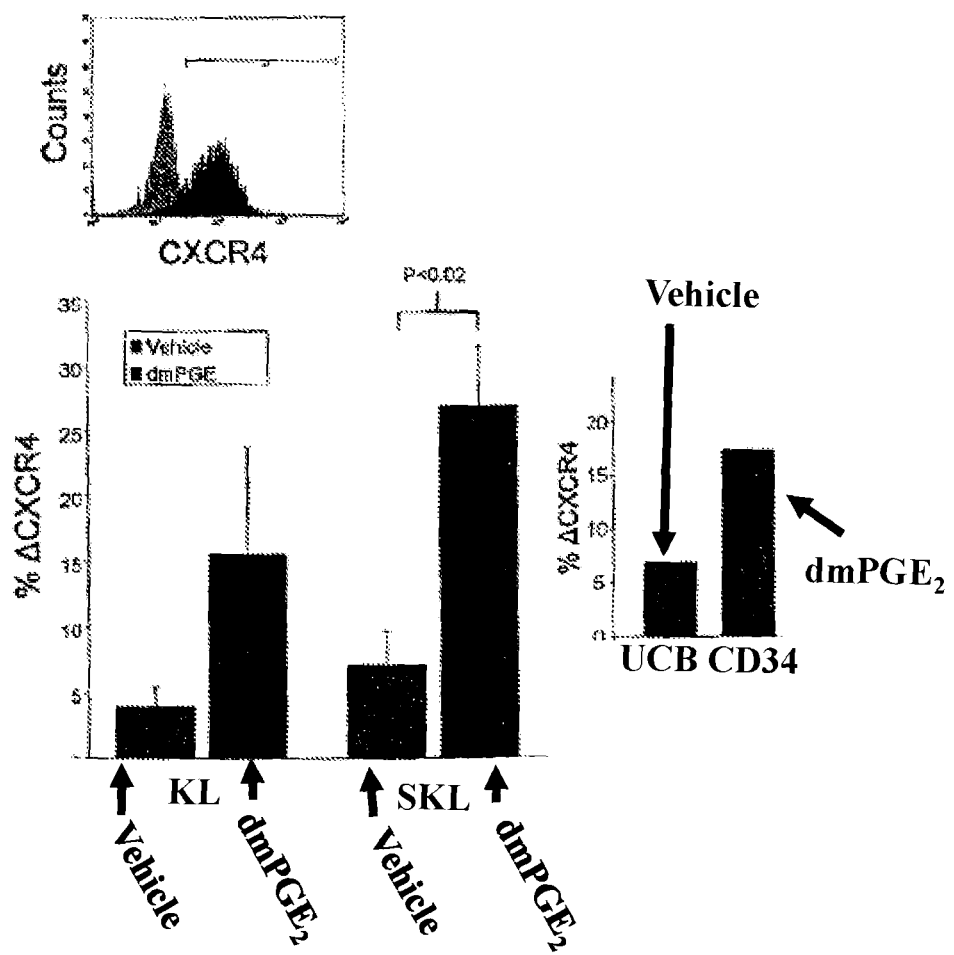

FIG. 4A. representative flow plot of CXCR4 receptor expression isotype control shown in gray (top row); Bar graph illustrating results of pulse exposure of murine and human HSPC to PGE$_2$ on CXCR4 expression, change in CXCR4 plotted for different conditions (bottom row).

Figure 4B:
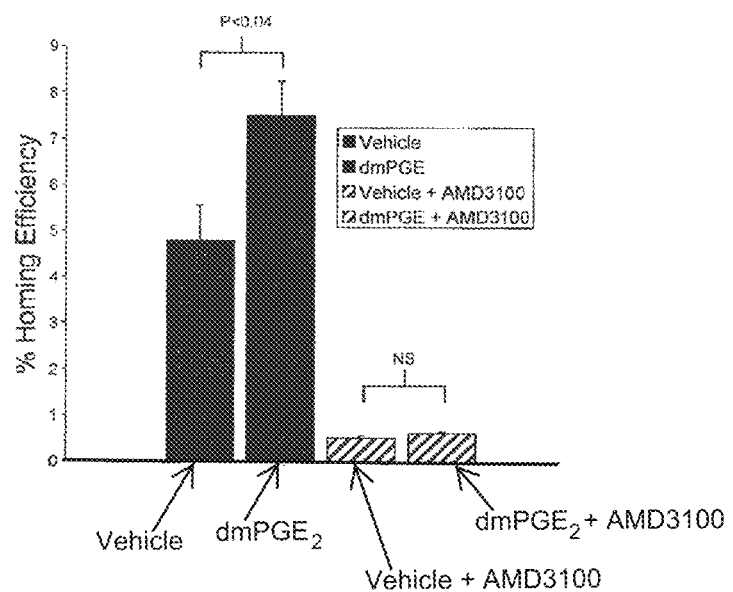

FIG. 4B. Bar graph of percent homing efficiency plotted for different treatments.

Figure 5A:
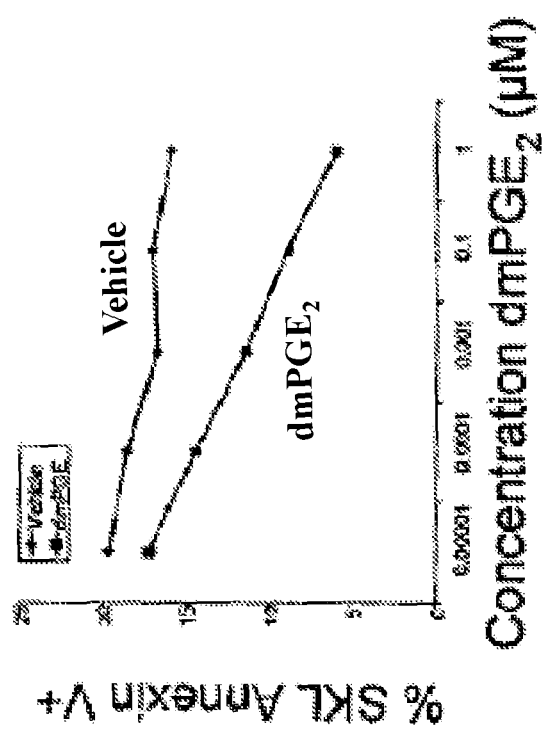

FIG. 5A. Percent of Annexin V+ SKL plotted as a function of dmPGE$_2$ concentration.

Figure 5B:
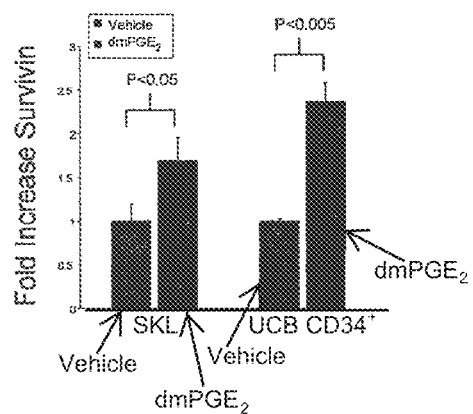

FIG. 5B. Fold increase in Survivin plotted for different conditions.

FIG. 5C. Percent change normalized to control activity plotted for different times of exposure to dm PGE$_2$.

Figure 6A:
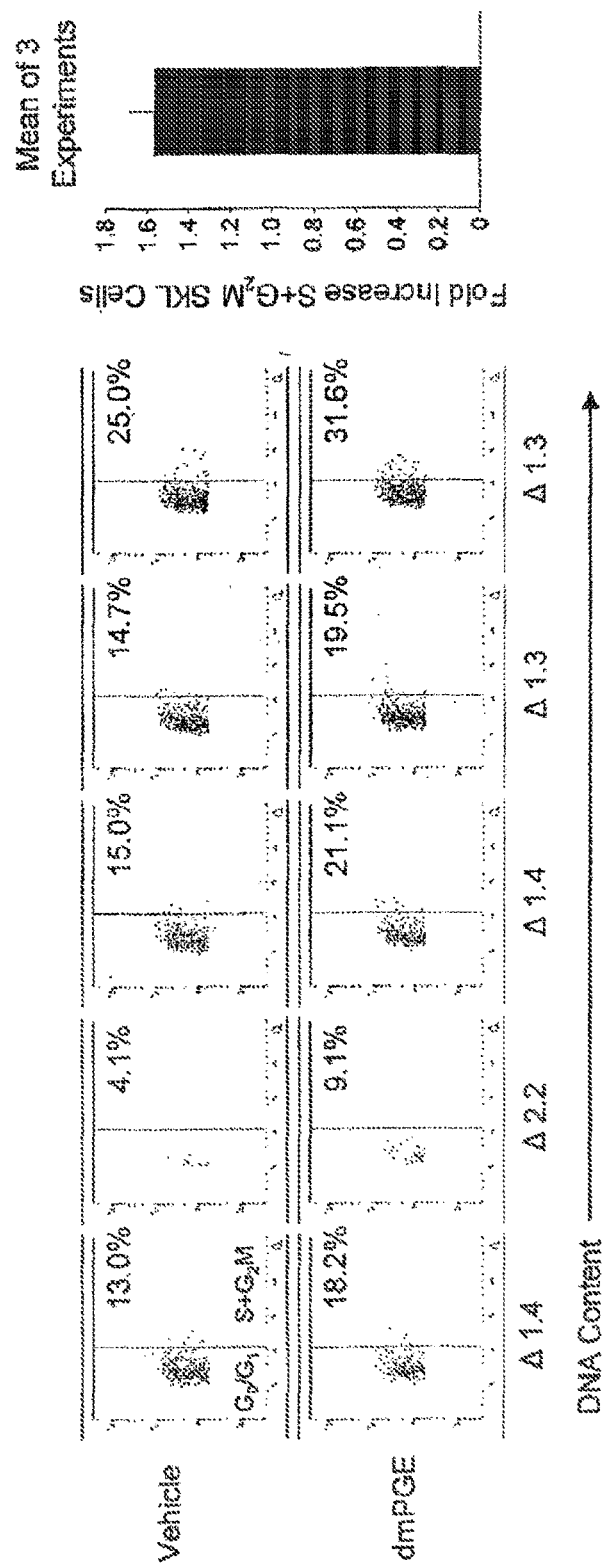

FIG. 6A. Representative flow plots showing DNA content (7AAD staining) of gated SKL cells, the percent of SKL in S+G2M phase, and the fold increase in cycling of dmPGEΣ-treated SKL (left panel); the chart shows combined data from 3 experiments (right panel).

Figure 6B:
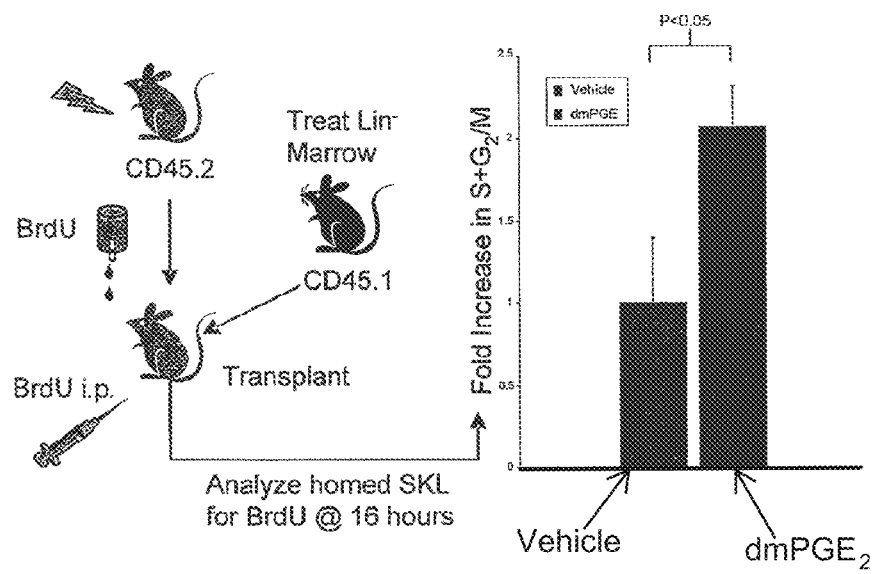

FIG. 6B. Outline of experiment and bar graph plotting of fold increase in homed SKL cells in S+G$_2$/M measured with different treatments. Cartoon showing experimental protocol (left panel); bar graph Fold Increase in S+G$_2$/M measured with and without dmPGE$_2$.

Figure 7A:
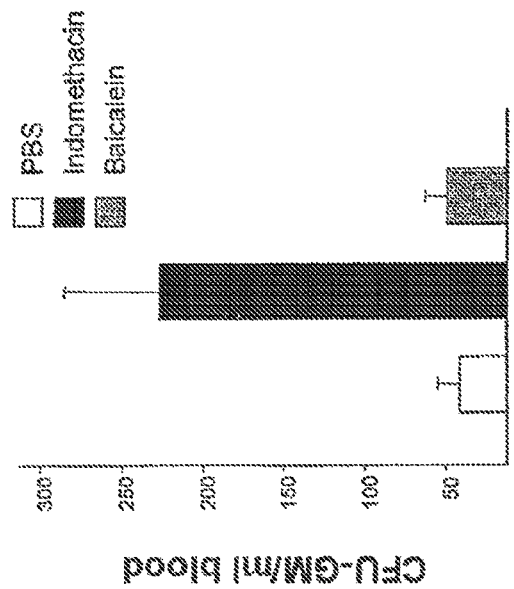

FIG. 7A. Bar graph plotting CFU-GM per mL of blood measured after different treatments.

Figure 7B:
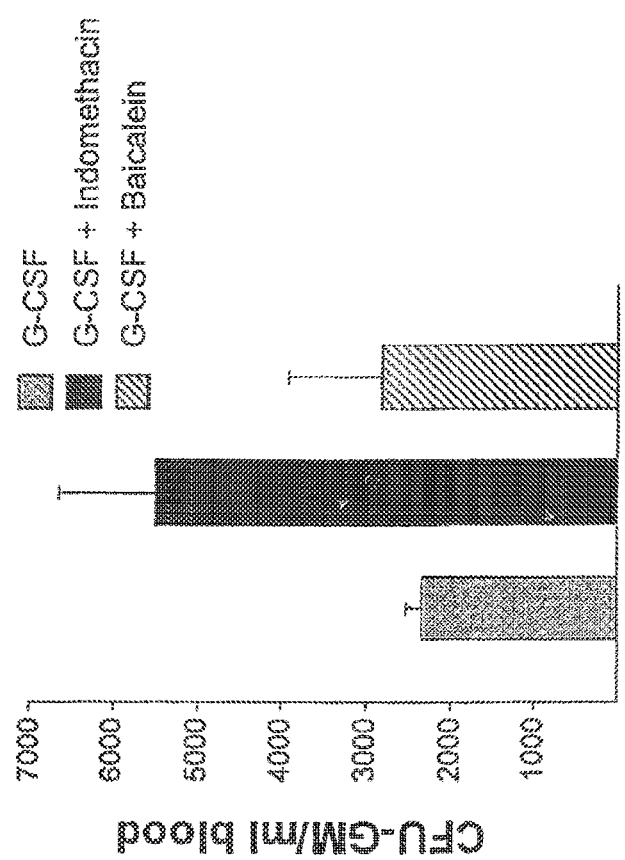

FIG. 7B. Bar graph plotting CFU-GM per mL of blood measured after different treatments.

FIG. 8. Table summarizing data illustrating that PGE$_2$ effects the cycling of SLAM SKL.

Figure 9:
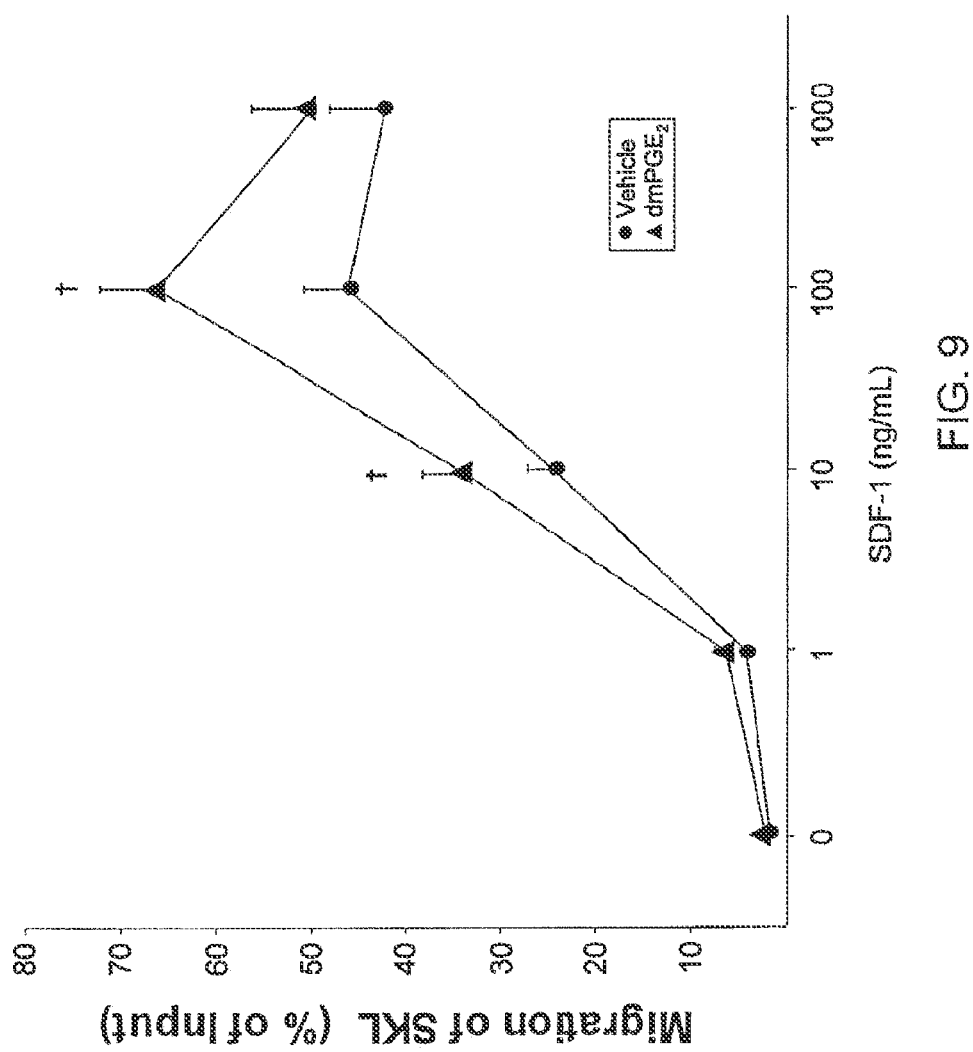

FIG. 9. Graph of migration control and dmPGE$_2$-treated cells versus SDF-1 concentration.

Figure 10:
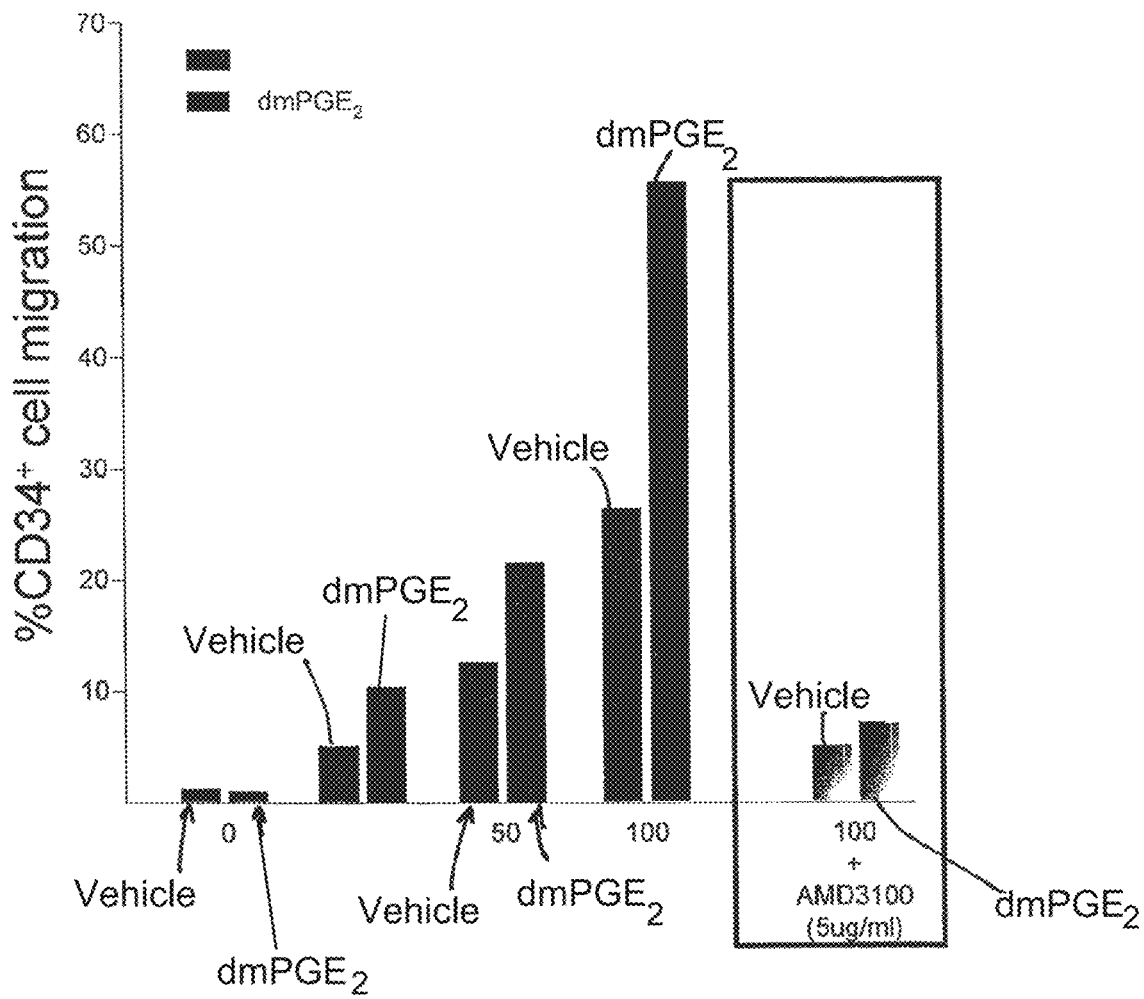

FIG. 10. Graph of percent CD34+ cell migration versus SDF-1 concentration and/or AMD3100 (1,1'-[1,4-Phenylenebis(methylene)]bis[1,4,8,11-tetraazacyclotetradecane]octohydrobromide dihydrate) marketed under the trade name MOZOBIL®.

Figure 11:
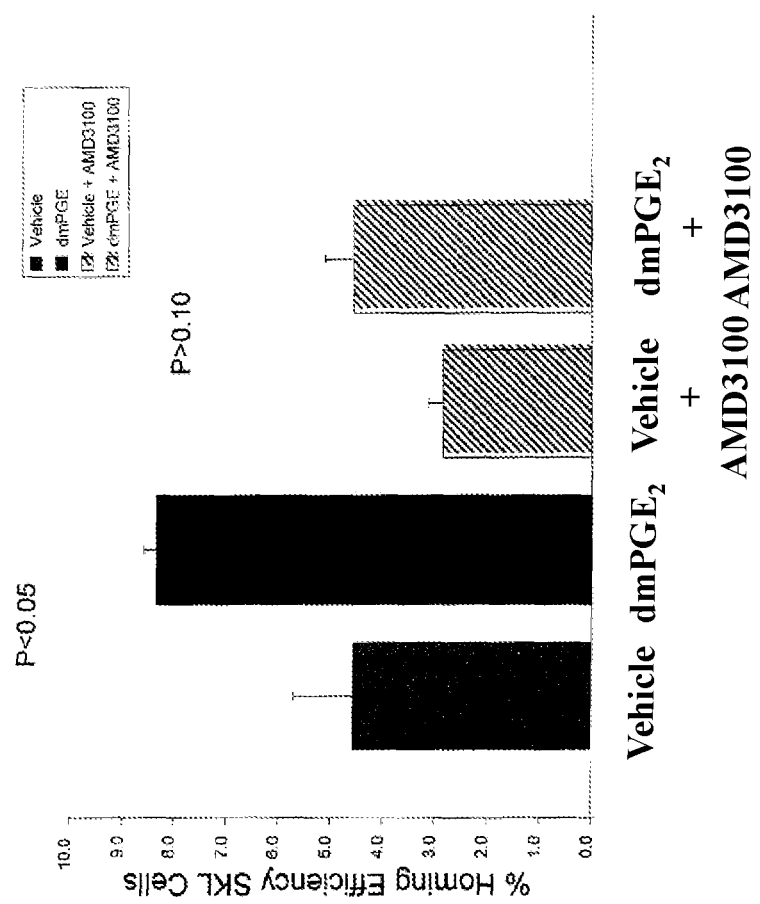

FIG. 11. Bar graph of percent homing efficiency of SKL cells versus treatment with dmPGE$_2$ and/or AMD3100 and various controls.

Figure 12:
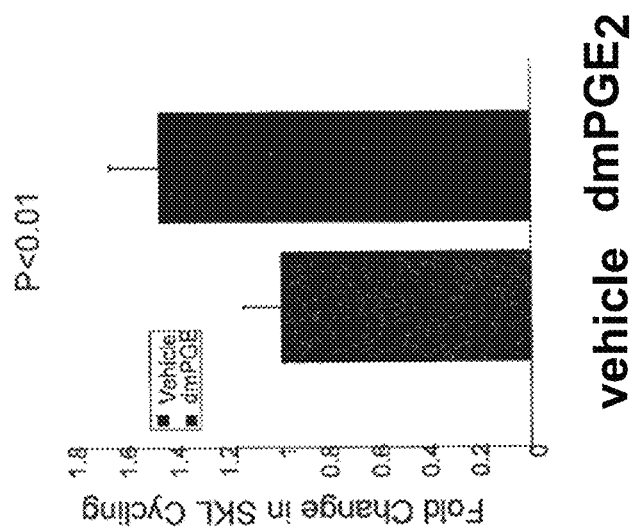
Figure 12:
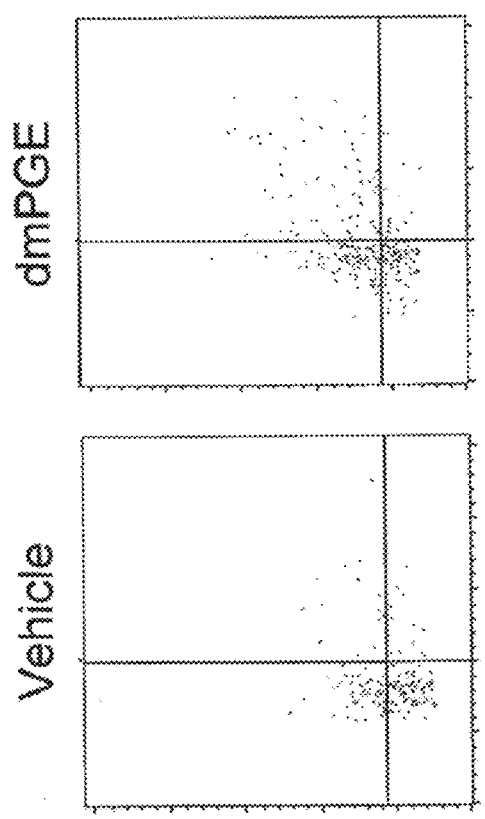

FIG. 12. FACS plot (left panel); and bar graph (right panel) illustrating Fold change in SKL cycling measured with and without dmPGE$_2$.

Figure 13:
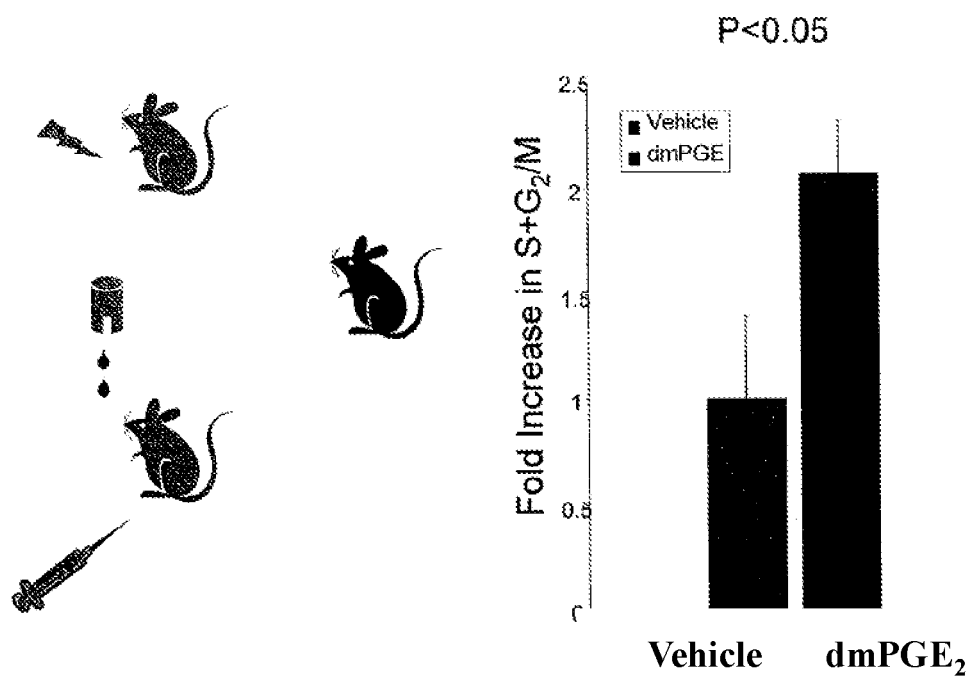

FIG. 13. Outline of a an experimental protocol (left panel); a bar graph showing an increase in S+G2/M measured with and without added dmPGE$_2$.

Figure 14:
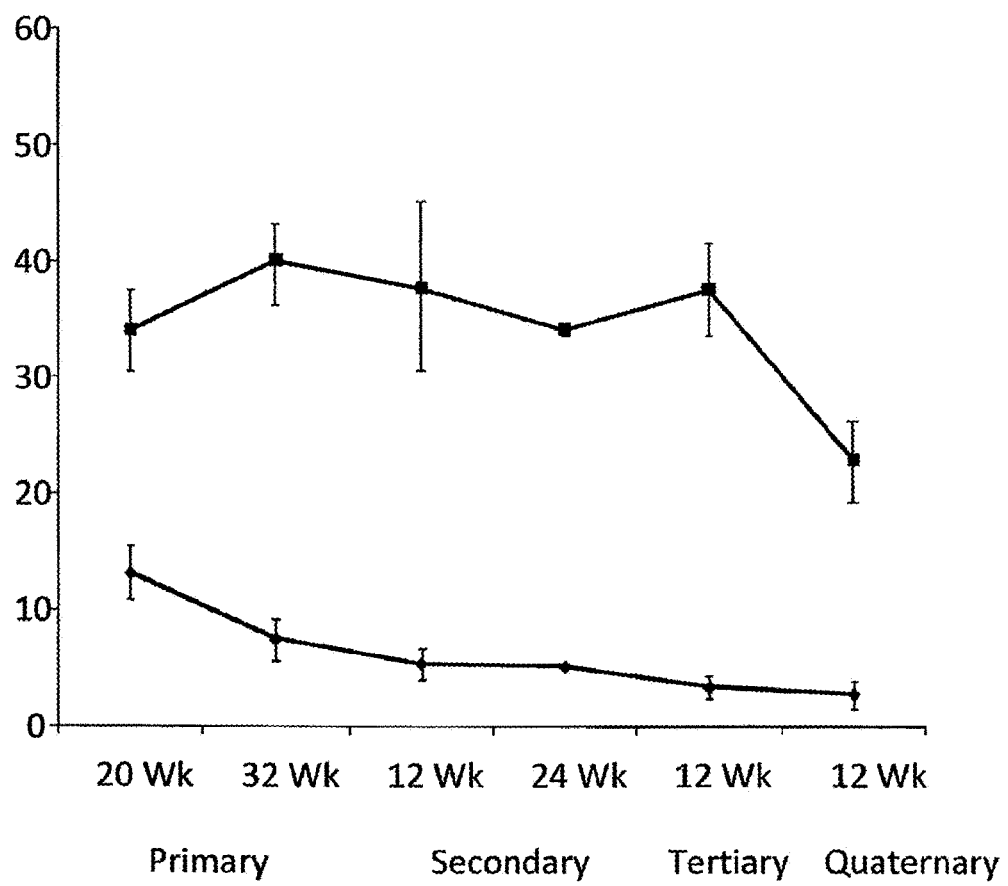

FIG. 14. Graph of percent chimersim measured in serial transplants over time after initial exposure to dmPGE$_2$ (squares) or control (vehicle, diamonds).

Figure 15:
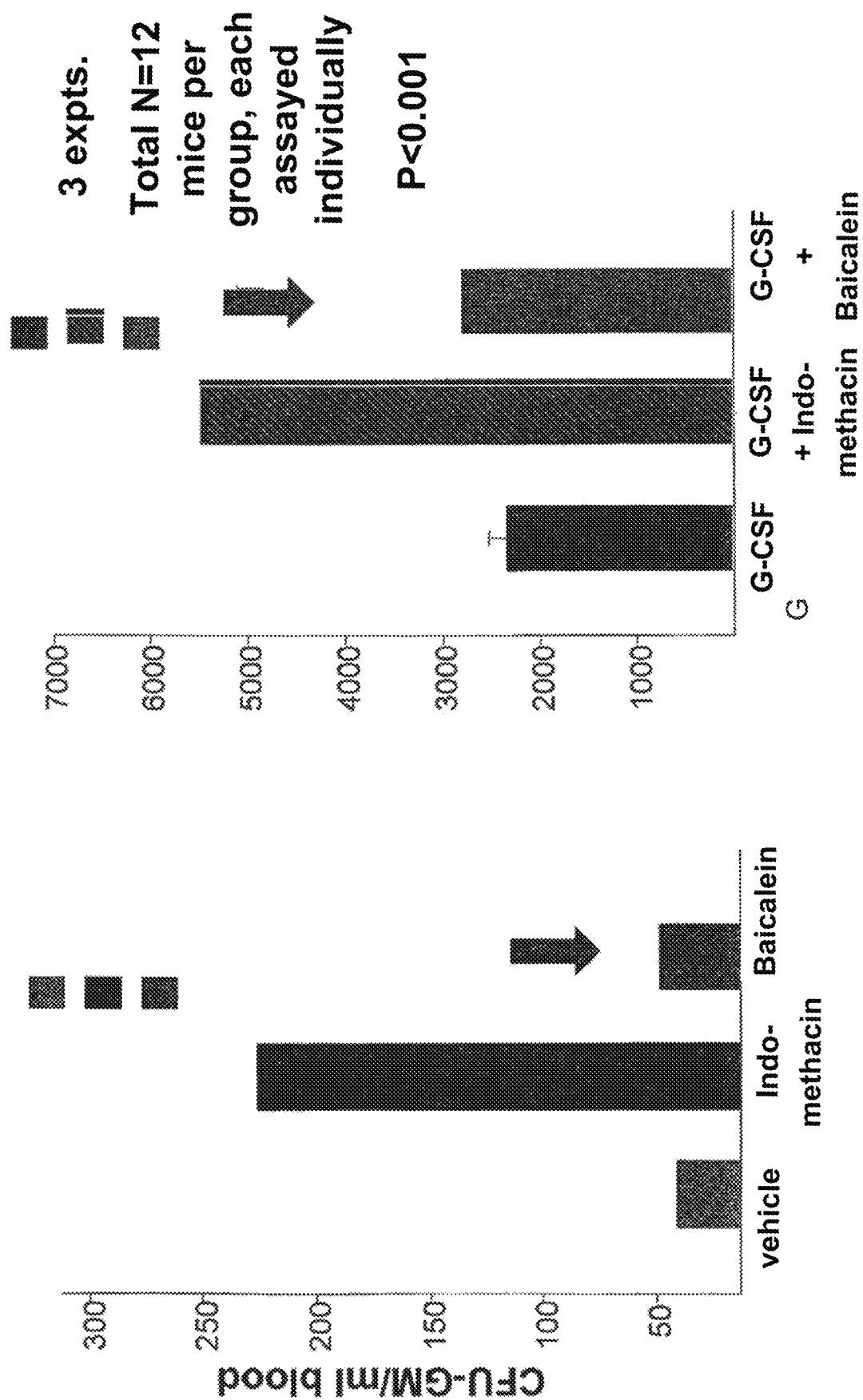

FIG. 15. Bar graph CFU-GM per ml of blood measured with vehicle (light gray) indomethacin (dark gray) or baicalein (gray) left panel; graph of data collected with G-CSF (light gray); G-CSF plus indomethacin (gray hatch) or G-CSF plus baicalein (gray).

Figure 16:
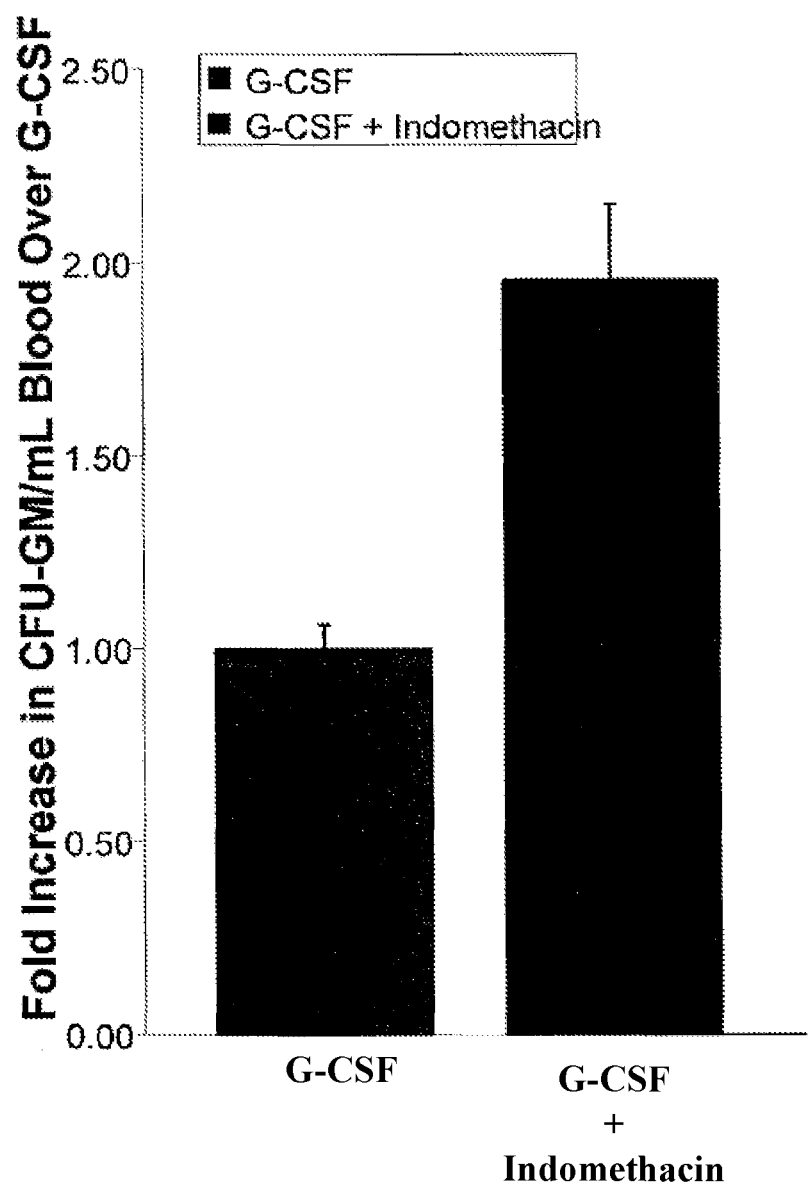

FIG. 16. Bar graph Fold Increase in CFU per ml of Blood over G-CSF measured with G-CSF and G-CSF plus indomethacin.

Figure 17:
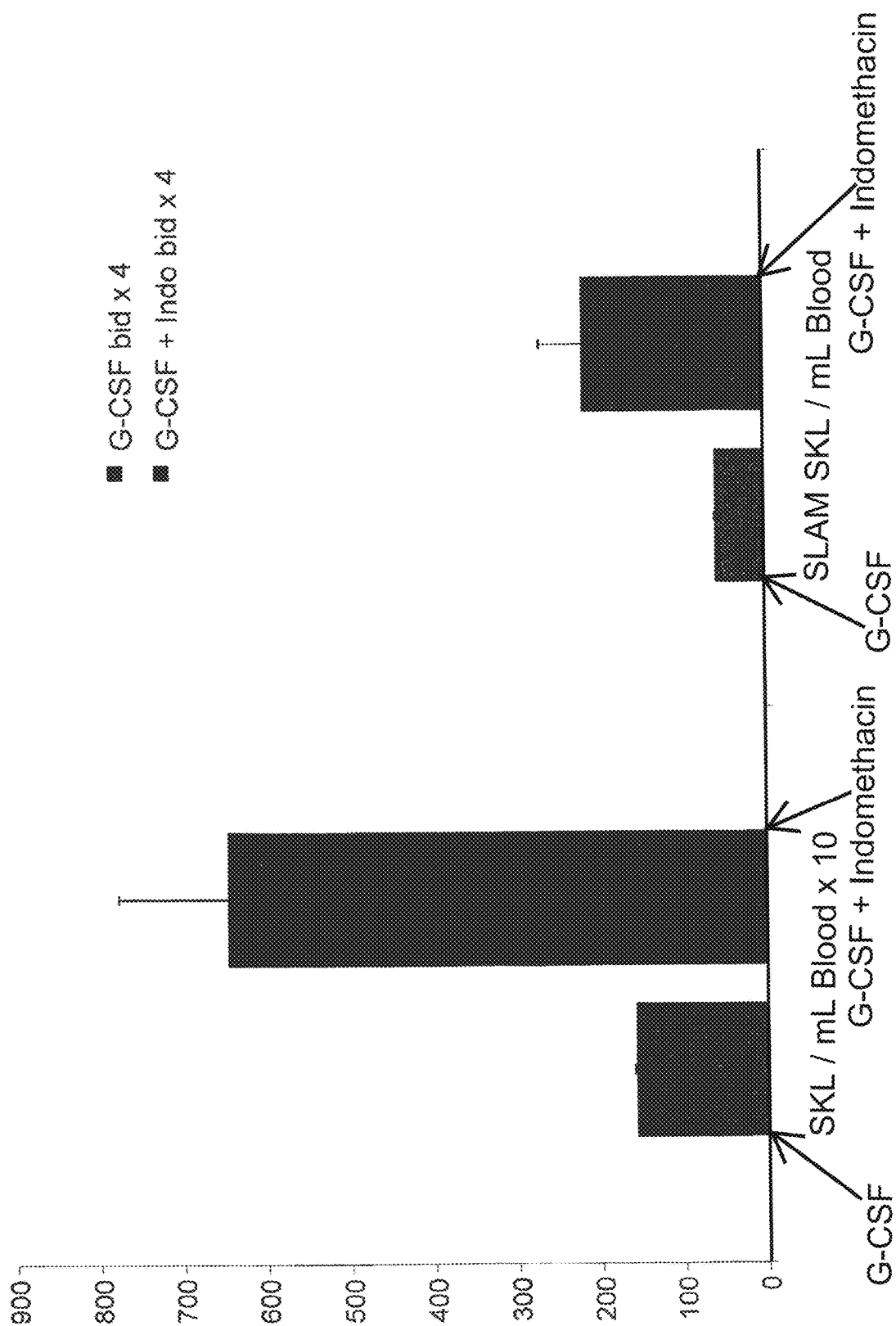

FIG. 17. Bar graph of phenotypic analysis of mobilized cells either SKL cells (left side) or SLAM SKL cells (right side) measured after treatment with either G-CSF or G-CSF plus indomethacin.

Figure 18:
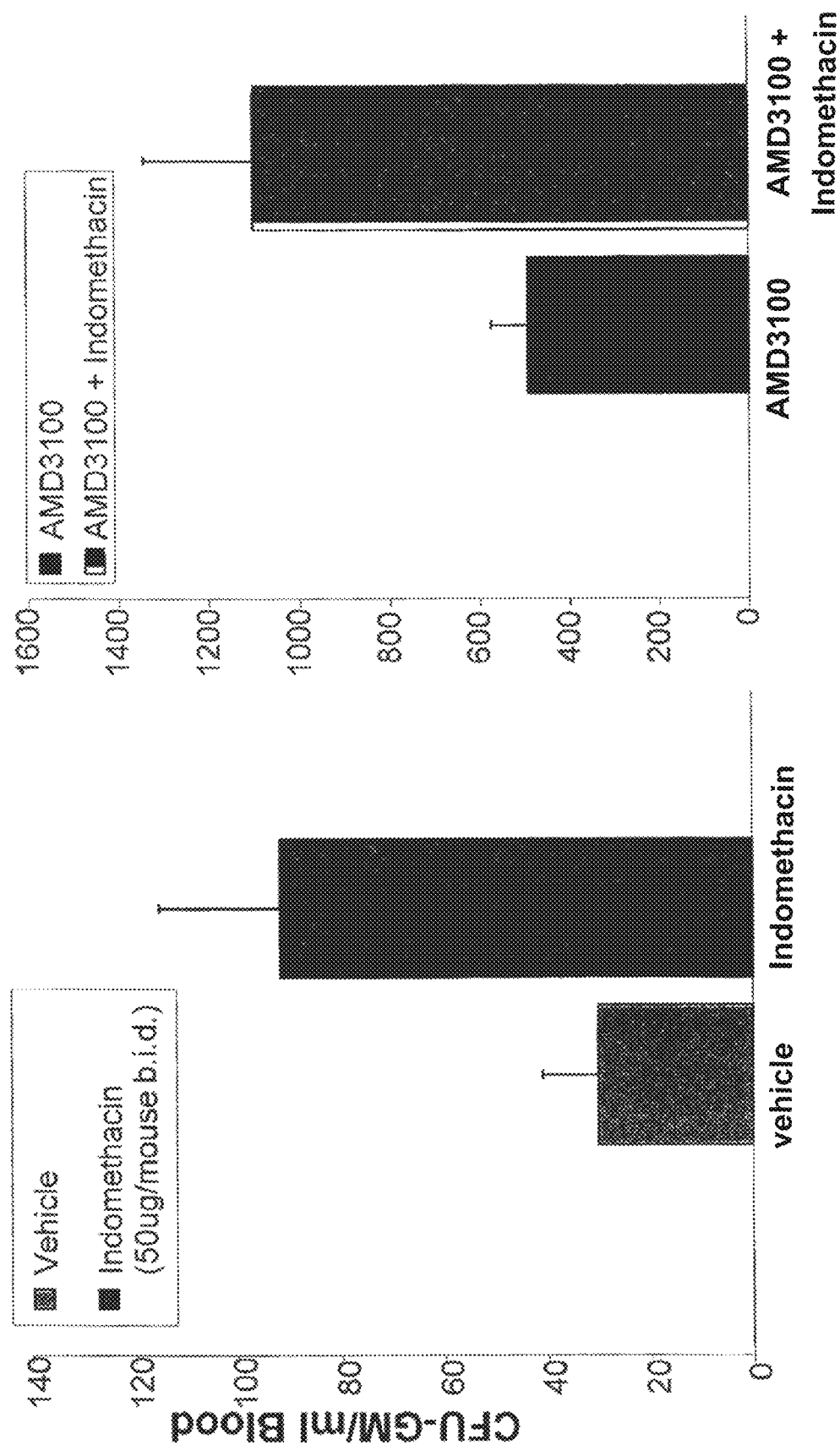

FIG. 18. Bar graph CFU-GM per ml of Blood plotted with either vehicle or indomethacin (left panel); or AMD3100 or AMD3100 plus indomethacin (right panel).

Figure 19:
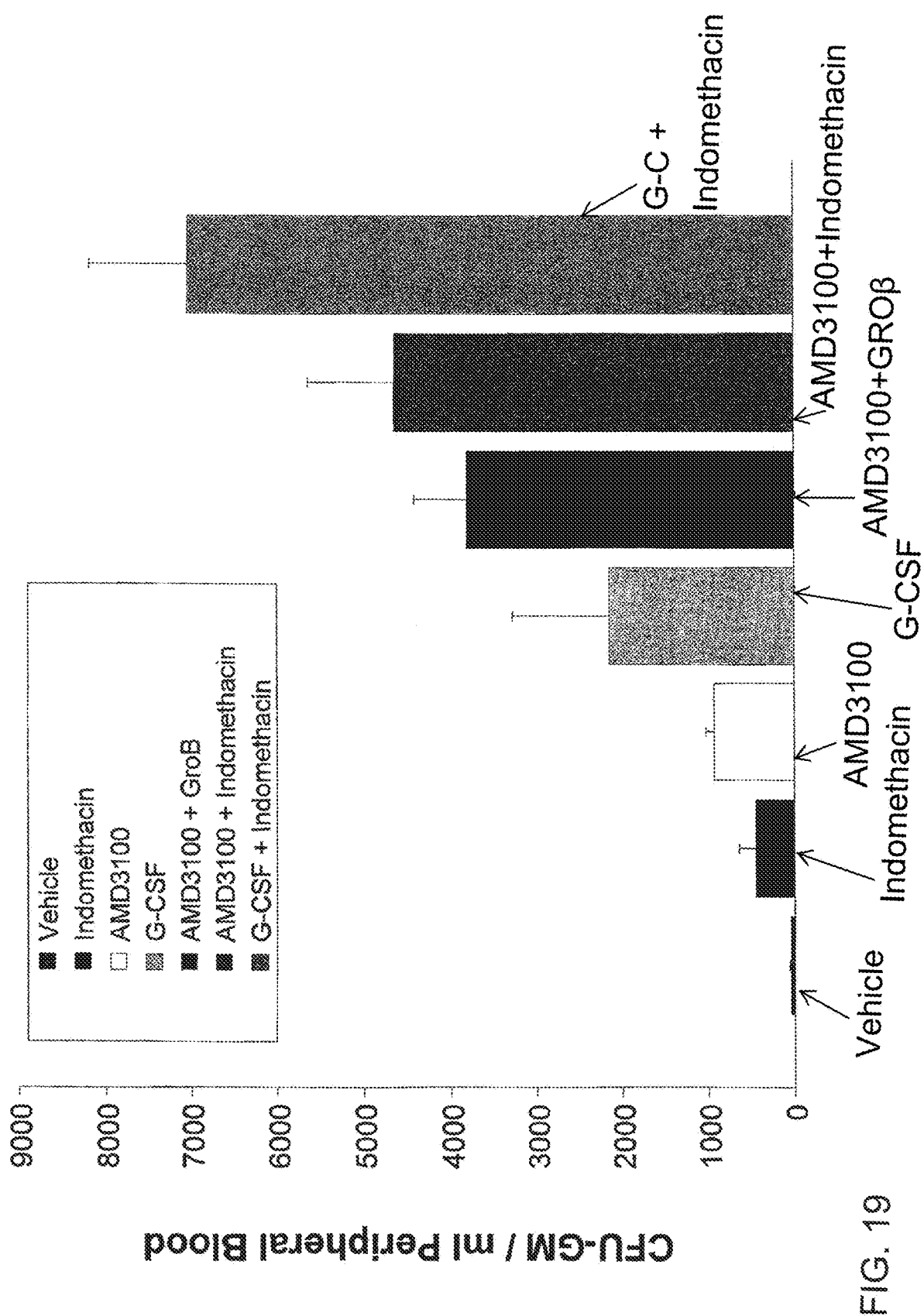

FIG. 19. Bar graph CFU-GM per ml of Peripheral Blood plotted measured after treatment with vehicle, indomethacin, AMD3100; G-CSF; AMD3100plus GROBeta; AMD3100 plus indomethacin or G-CSF plus indomethacin.

Figure 20:
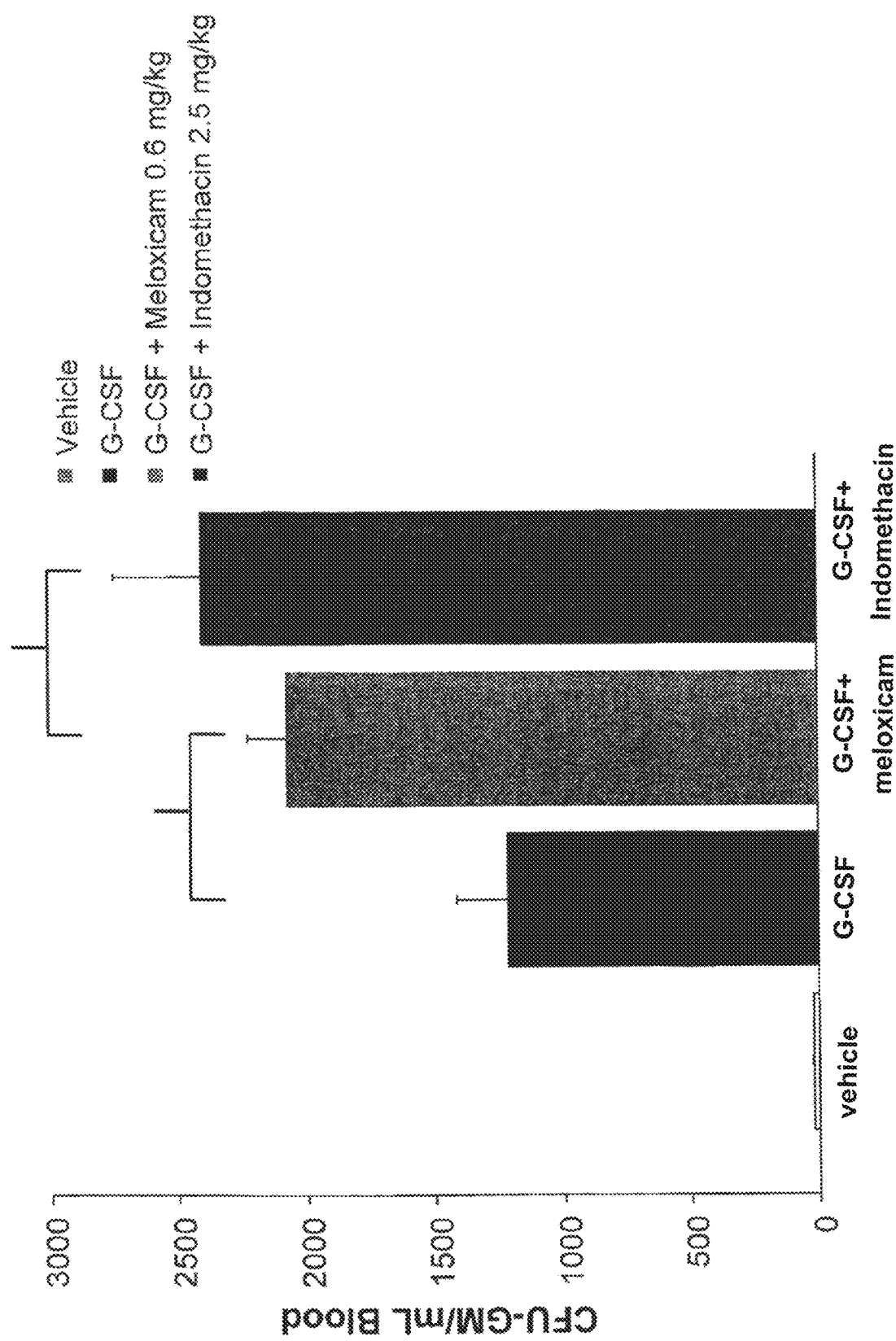

FIG. 20. Bar graph CFU-GM per ml of Blood after treatment with vehicle (clear), G-CSF (black), G-CSF plus meloxicam ((8E)-8-[hydroxy-[(5-methyl-1,3-thiazol-2-yl)amino] methylidene]-9-methyl-10,10-dioxo-10$\lambda^6$-thia-9-azabicyclo[4.4.0]deca-1,3,5-trien-7-one) (light gray), or G-CSF plus indomethacin (gray).

Figure 21:
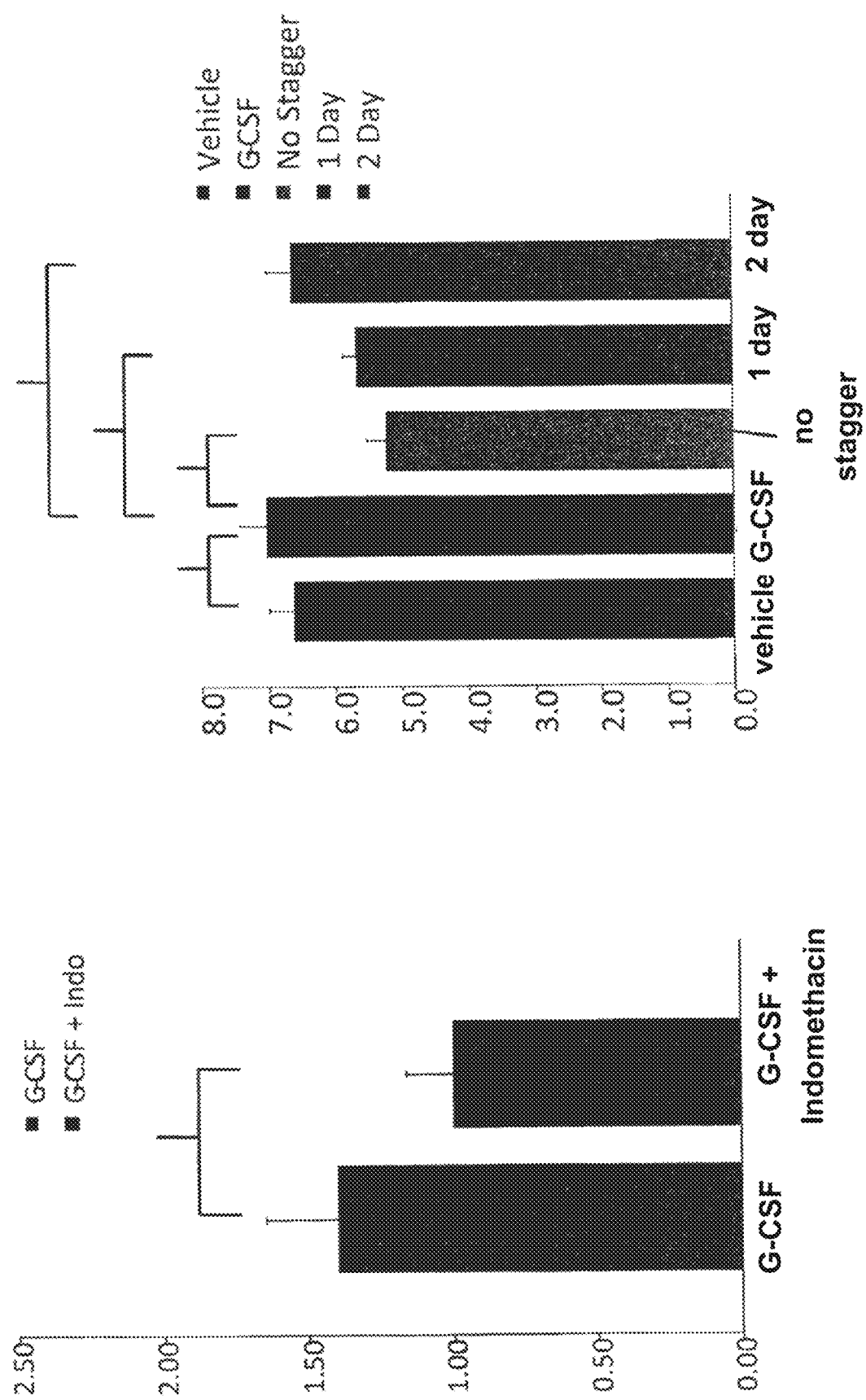

FIG. 21. Bar graph Competitive Repopulating units measured with either G-CSF (light gray) or G-CSF plus indomethacin (gray) (left panel); and MFI CXCR4 on SKL cells measured with vehicle, G-CSF; no Stagger, 1 day stagger or 2 day stagger (right panel).

Figure 22:
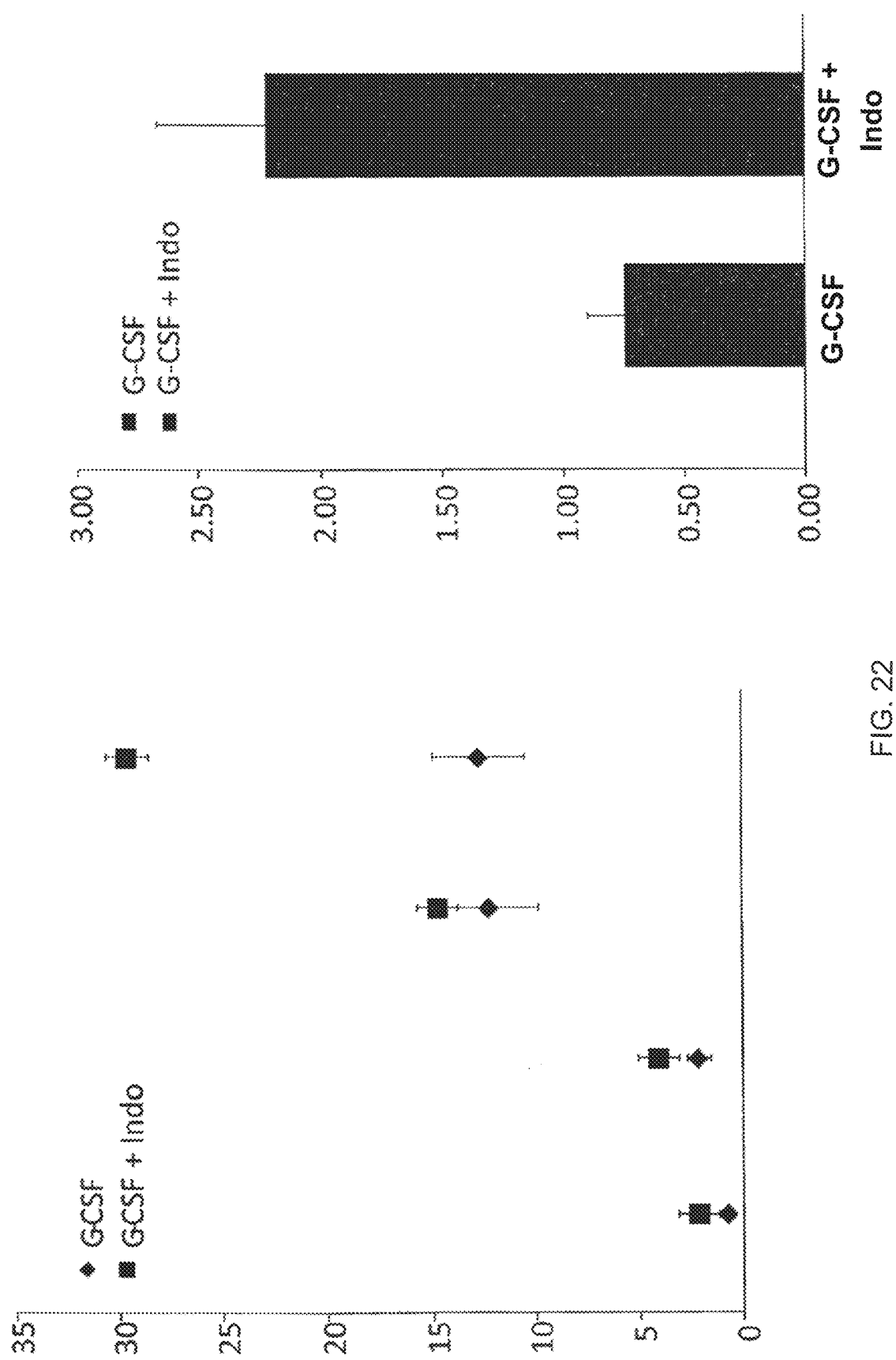

FIG. 22. Graph of percent Chimerism versus PBMC: BM ratio measured with either G-CSF (diamonds) or G-CSF plus indomethacin (squares) (left panel); CRU scaled to 2 million PBMC measured with either G-CSF (light gray) or G-CSF plus indomethacin (gray).

Figure 23:
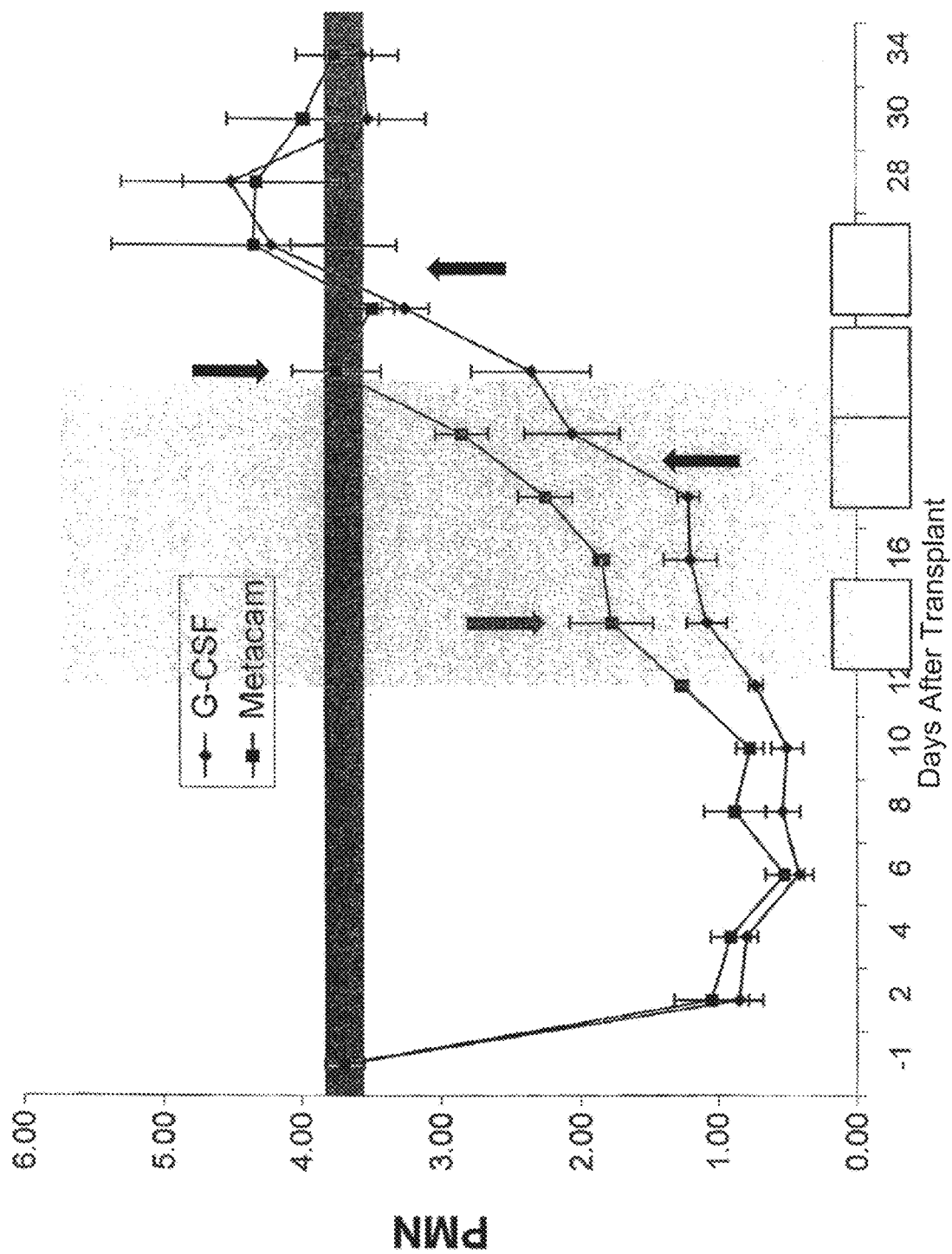

FIG. 23. Graph of PMN versus days after transplant of PBMC mobilized by G-CSF (diamonds) or G-CSF plus Metacam (meloxicam)(squares).

Figure 24:
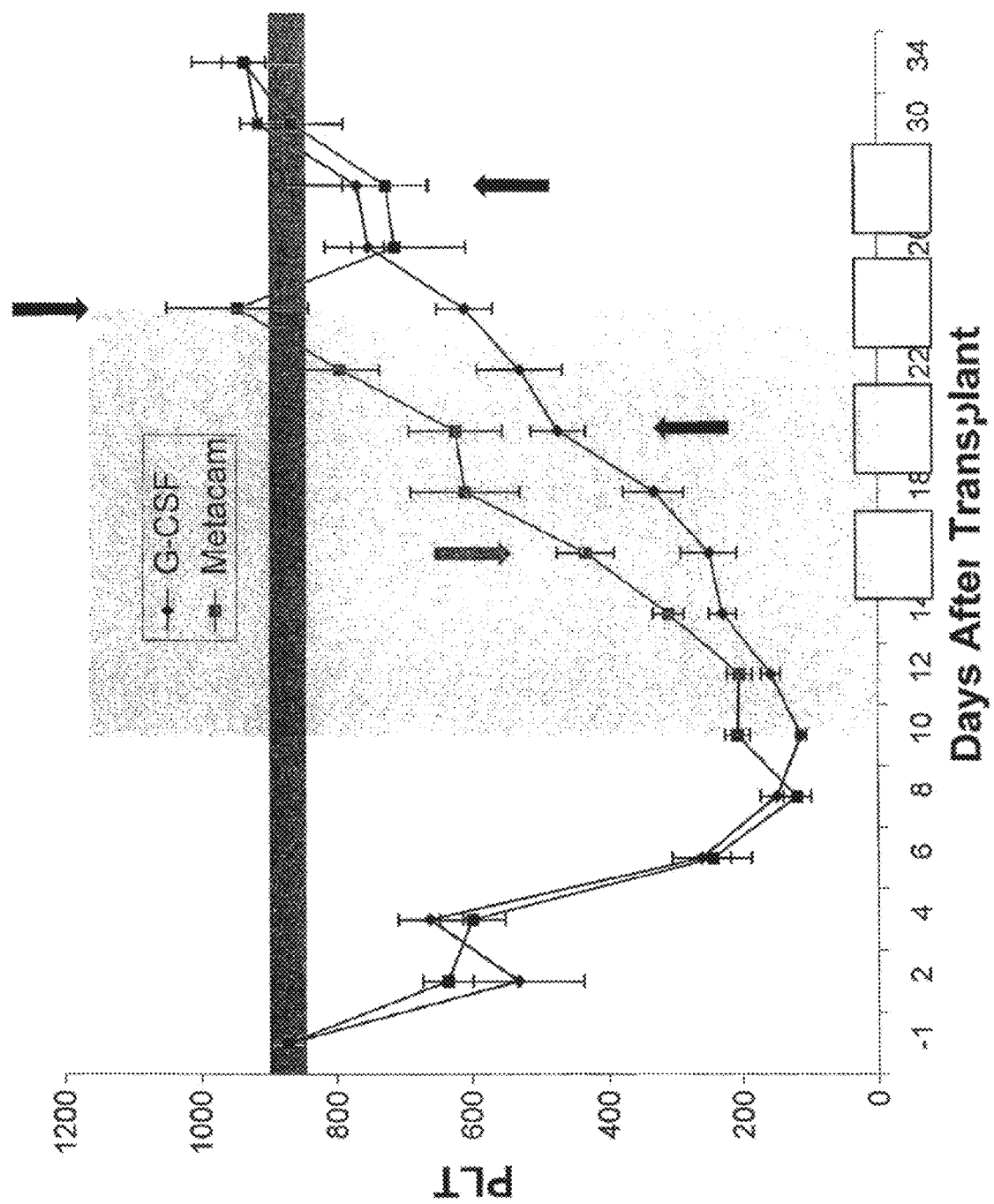

FIG. 24. Graph of PLT versus days after transplant of PBMC mobilized by G-CSF (diamonds) or G-CSF plus Metacam (meloxicam)(squares).

Figure 25:
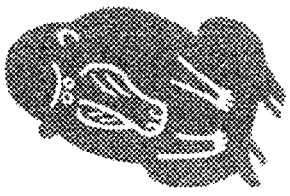
Figure 25:
Figure 25:

FIG. 25. Cartoon summarizing experiment designed to test the effect of treating baboons with either G-CSF alone or G-CSF plus meloxicam.

Figure 26:
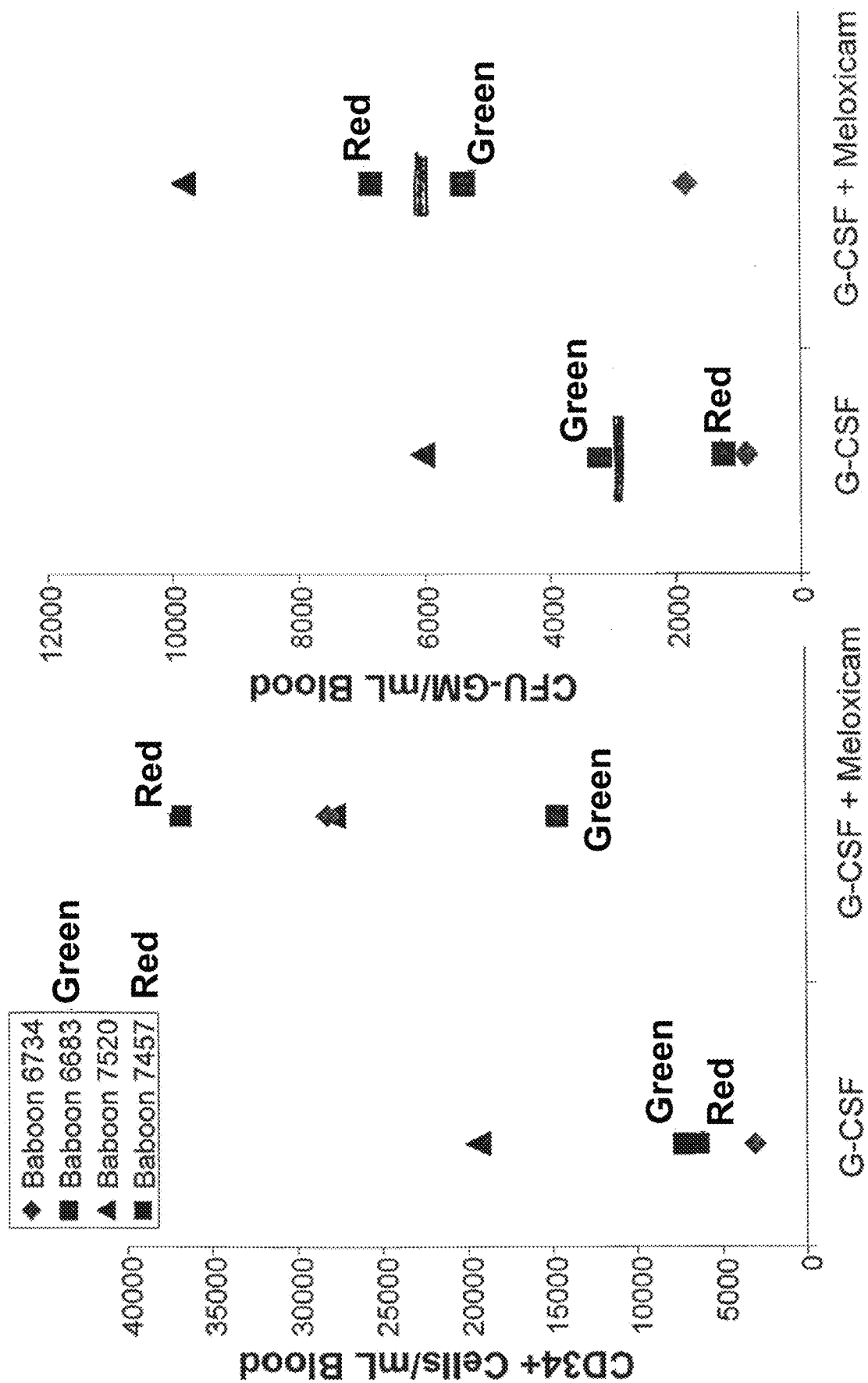

FIG. 26. Plots of CD34+ Cells (left side) or CFU-GM (right side) per mL of blood drawn from 4 different baboons treated with either G-CSF or G-CSF plus meloxicam.

Figure 27:
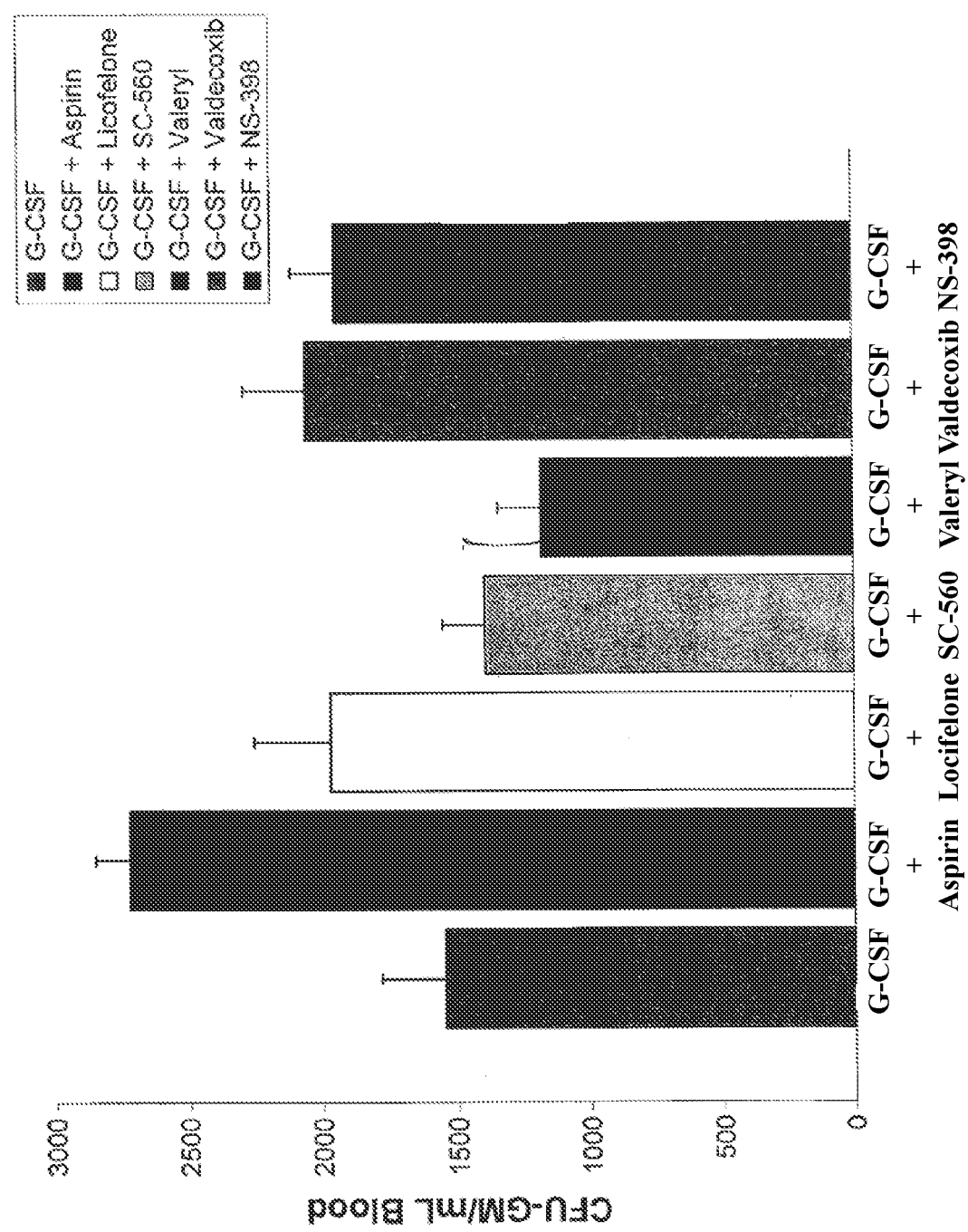

FIG. 27. Bar graph CFU-GM per mL of blood tested using different compounds that vary in their selectivity for either COX-1 or COX-2.

Figure 28:
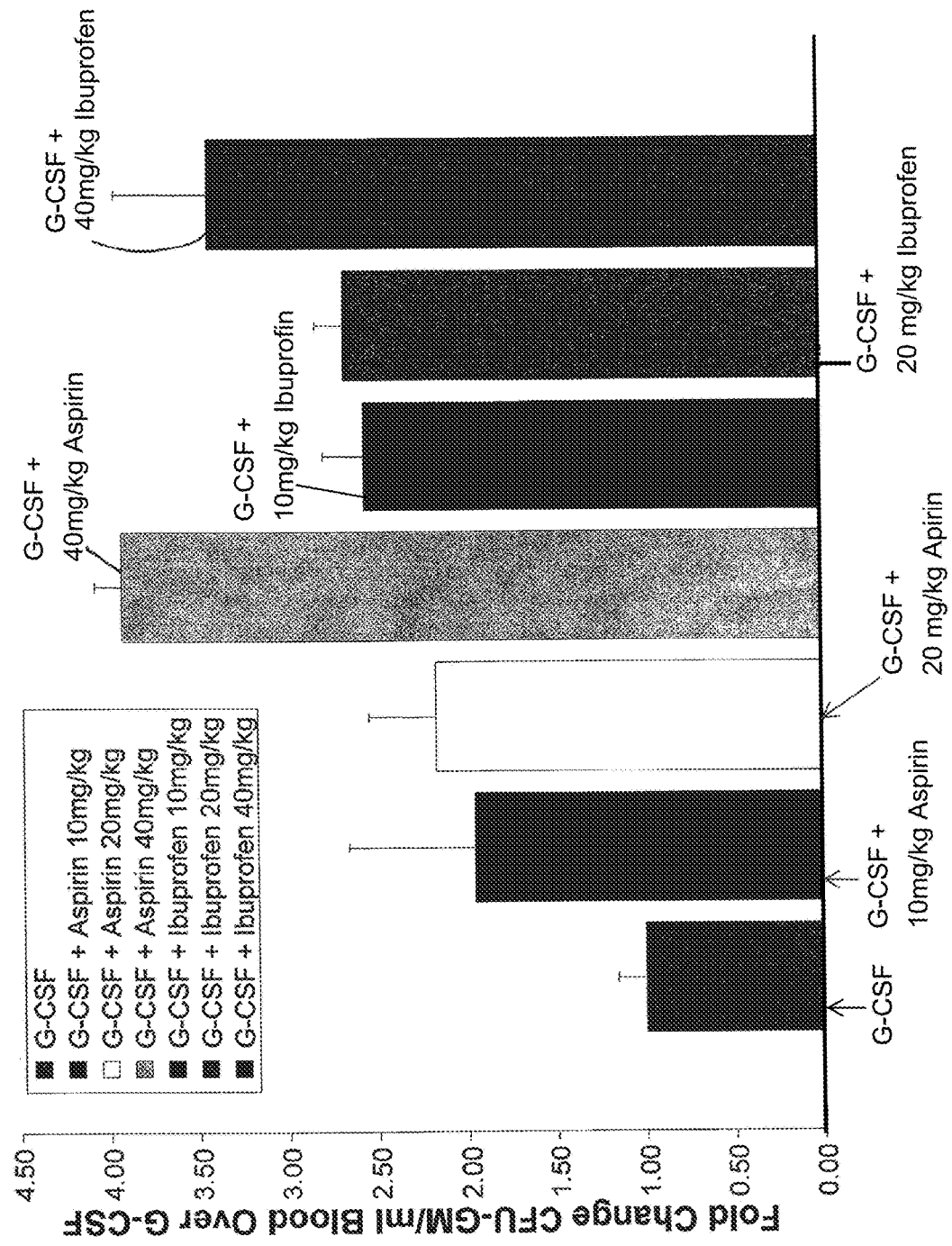

FIG. 28. Bar graph of Fold Changes in CFU-GM over G-CSF per mL of blood tested after treating cells with G-CSF or G-CSF plus different amounts of either aspirin or ibuprofen.

Figure 29:
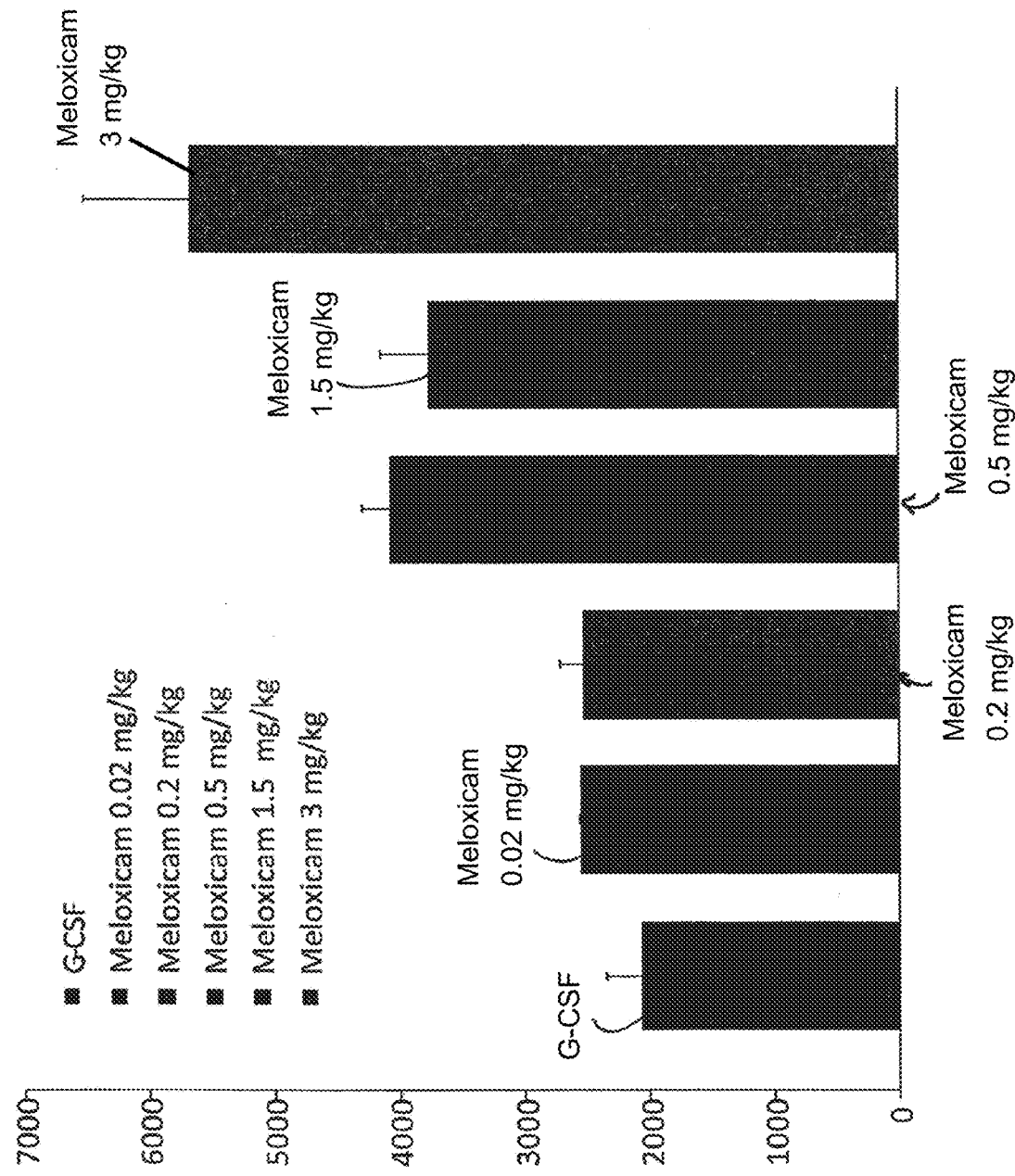

FIG. 29. Bar graph CFU-GM per mL of blood measured in the peripheral blood after treatment with either G-CSF or different levels of meloxicam.

Figure 30:
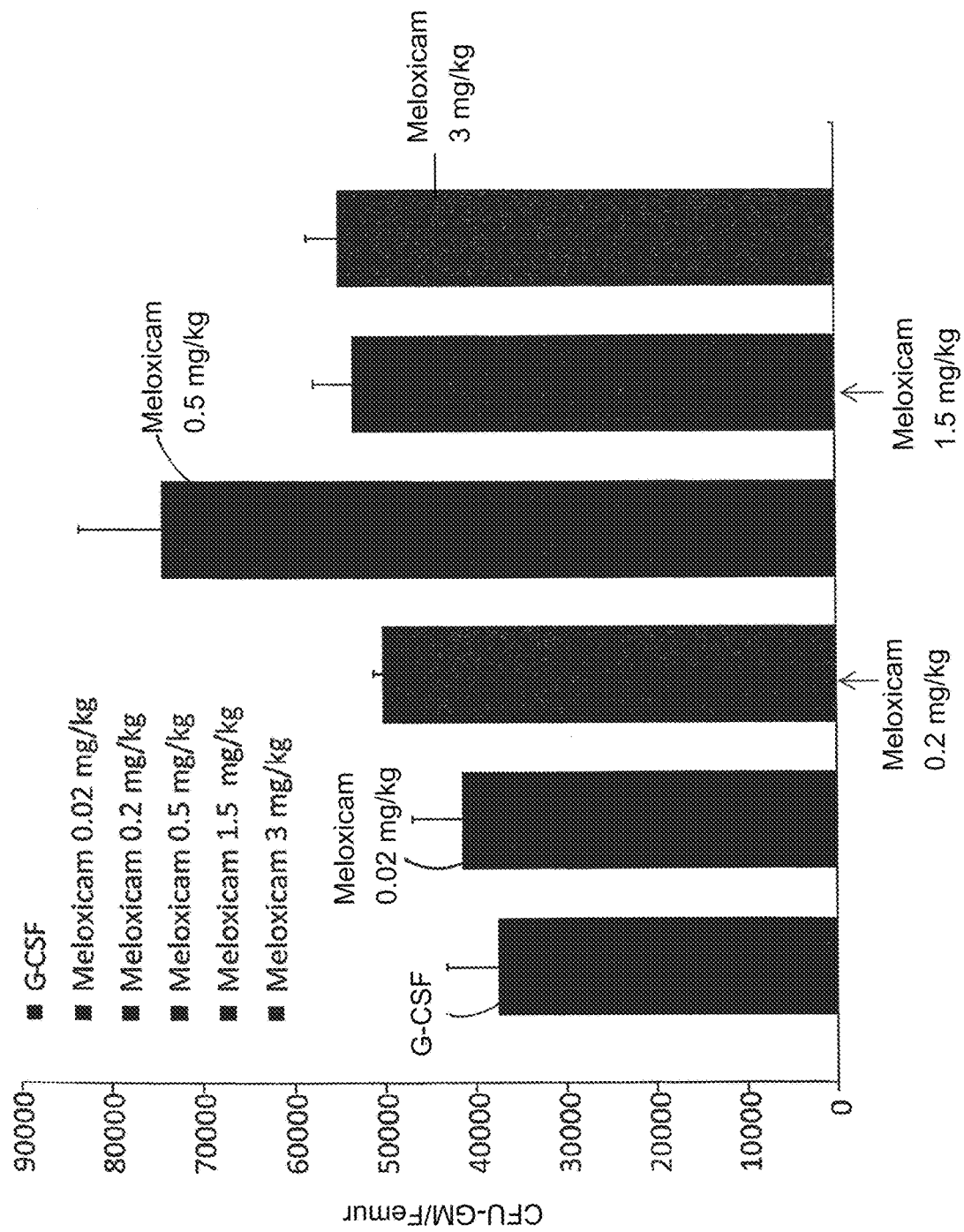

FIG. 30. Bar graph CFU-GM per Femur measured in bone marrow after treatment with either G-CSF or different levels of meloxicam.

DETAILED DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Prostaglandin E2 (PGE2) is an abundant physiological eicosanoid and a known mediator of cancer, inflammation, and numerous other physiological systems. The roles for $PGE_2$ in hematopoiesis have been explored by various research teams, but the outcomes are difficult to reconcile. For example, in vitro and in vivo studies demonstrate that $PGE_2$ can negatively regulate myelopoiesis: $PGE_2$ promotes BFU-E and CFU-GEMM colony formation and enhances proliferation of CFU-S and CFU-GM. On the other hand, $PGE_2$ can stimulate HSPC and have biphasic effects on hematopoiesis: Short-term ex vivo $PGE_2$ treatment of marrow cells was shown to stimulate the production of cycling human CFU-GM from a population of quiescent cells, possibly stem cells or more primitive progenitor cells. Further, recently, it was shown that ex vivo exposure to 16,16-dimethyl $PGE_2$ increased the repopulating capacity of murine bone marrow cells and kidney marrow recovery in zebrafish (North et at, 2007). These studies implicate $PGE_2$ in the regulation of hematopoiesis, but fail to link $PGE_2$ to hematopoietic stem cell homing. Rather, the previous studies tend to indicate $PGE_2$ is involved in modulation of HSPC differentiation, and $PGE_2$ has no direct effect on cell homing.

As demonstrated herein $PGE_2$ has direct and stabilizing effects on long-term repopulating HSPC and facilitates engraftment by enhancing survival, homing, and proliferation of self-renewing HSPC.

One aspect disclosed herein is the inhibition of cyclooxygenase activity which increases the frequency of hematopoietic stem and progenitor cell circulation in the peripheral blood system. In one non-limiting example, administration of cyclooxygenase inhibitors, for example, 50 micrograms of indomethacin daily, by oral or systemic routes to hematopoietic donors one day prior to and with each day they receive a dose of mobilizing agent, enhanced the mobilization of stem cells and progenitor cells in the periphery. Concurrent use of cyclooxygenase inhibitor, for example, Indomethacin, with clinically approved mobilizing agent, for example, G-CSF, produces a synergistic effect to mobilize progenitor cells.

The mobilization of hematopoietic stem cell and progenitor cell can also be achieved by providing the donor with an effective amount of a prostaglandin E receptor antagonist.

Some aspects disclosed show that ex vivo exposure to $PGE_2$ enhances HSPC frequency after transplantation and provides a competitive advantage for $PGE_2$-treated HSPC. Treating bone marrow stem cells with $PGE_2$ ex vivo enhances total stem cell engraftment in mice, resulting in enhanced stem cell survival, increased stem cell homing efficiency and increased stem cell self-renewal. Enhancement of HSPC frequency induced by dmPGE$_2$ was demonstrated by using a limiting dilution competitive transplantation model that compared engraftment of control and dmPGE$_2$-treated cells in direct head-to-head analysis within the same animal. For example, un-treated hematopoietic grafts or purified hematopoietic stem cell populations (e.g., SKL cells in mice or CD34+ cells in humans) were incubated with authentic $PGE_2$ or the more stable analog 16,16-dimethyl $PGE_2$ (or any additional active PGE analogue) on ice at concentrations of 0.001-10 microMolar $PGE_2$ per 1-10 million cells in 1 ml of culture medium, e.g. IMDM, for 1-6 hrs. After incubation, the cells were washed 3 times in sterile saline and administered to recipients, intravenously. This process demonstrated a ~4-fold competitive advantage of $PGE_2$-pulsed HSPC based upon calculation of HSPC frequency by Poisson statistics and analysis of competitive repopulating units (CRU). Frequency analysis demonstrates equivalent reconstitution using one-fourth the number of $PGE_2$ treated cells vs. control cells. In addition, full hematopoietic reconstitution was observed in secondary transplant recipients using either control or $PGE_2$-treated cells, indicating no adverse impact of $PGE_2$ on HSPC self-renewal. In fact, a trend towards increased LTRC activity was seen, indicating that the enhancing effect of short-term $PGE_2$ exposure on HSPC observed in primary transplants was long lasting, since no additional treatment was performed on cells or animals before serial-transplant. Enhanced engraftment of $PGE_2$-treated cells was stable over 28 weeks. Analysis in secondary transplanted animals 90 days post-transplant demonstrated full multi-lineage reconstitution and continued higher HSPC frequency, indicating a stable effect of short-term $PGE_2$-treatment on long-term repopulating HSPC.

Enhanced engraftment can result from changes in HSPC frequency, homing, survival and/or proliferation. It was suggested by North, et.al. that $PGE_2$ did not affect HSPC homing; however, their studies did not specifically assess HSPC. Unexpectedly, as demonstrated herein the $PGE_2$-induced enhanced HSPC frequency was stable throughout a >20 week period and was maintained in secondary transplants. Direct comparison in competitive transplant models showed that short-term exposure of HSPC to $PGE_2$ produced a ~4-fold competitive advantage. Although total transplanted cells had no difference in homing efficiency between control and $PGE_2$-treated cells, enhanced homing efficiency of $PGE_2$-treated, sorted SKL cells was observed, strongly suggesting $PGE_2$ has a direct effect on HSPC homing.

These results suggest $PGE_2$'s greater effect for HSPC or HSPC long term repopulation ability, rather than only a short term effect as proposed by previous studies.

One possibility, offered by way of explanations and not limitation, is that the effects of $PGE_2$ on HSPC function might be mediated through upregulation of the alpha-chemokine receptor CXCR4 chemokine receptor, implicated in HSPC homing and self-renewal, and the inhibitor of apoptosis protein Survivin, which regulates HSPC survival and proliferation.

Flow cytometry and QRT-PCR shows expression of all 4 $PGE_2$ receptors (EP1-EP4) on Sca-1$^+$, c-kit$^+$, Lineage$^{neg}$ (SKL) murine marrow cells and on CD34$^+$ human cord blood cells (UCB) with no overt differences in receptor subtype expression. When analyzing several functional properties relevant to HSPC function, a significant increase in CXCR4 expression on both SKL (26.8%) and CD34$^+$ UCB (17.3%) was seen after $PGE_2$ exposure, with significant upregulation of CXCR4 mRNA at ~6 hours post-exposure. Increased CXCR4 was coincident with an ~2-fold increase in in vivo marrow homing efficiency of $PGE_2$-treated grafts and was observed with un-manipulated bone marrow (p<0.001, 3 expts, n=6 mice/group/expt, assayed individually) and with purified SKL cells in head-to-head competition in the same animal (p<0.001, 2 expts, n=5 mice/group/expt, assayed individually), indicating a direct effect Of $PGE_2$ on HSPC. The increase in homing efficiency was significantly reduced by treatment with the selective CXCR4 antagonist AMD3100.

$PGE_2$ treatment increased SKL cell CXCR4 mRNA and surface expression. In addition, the CXCR4 antagonist AMD3100 significantly reduced the enhancing effect of $PGE_2$ on homing, suggesting that enhanced CXCR4 expression and chemo-attraction to marrow SDF-I is largely responsible for enhanced homing, although additional effects on adhesion molecule expression or function cannot be excluded.

One aspect disclosed herein, is that $PGE_2$ treatment of a recipient enhances survival of stem cells transplanted into recipients in vivo. Parenteral administration of $PGE_2$ or active analogs to recipients at the time of transplant and to continue daily administration to enhance stem cell might increase the survival of transplanted HSPC. For example, $PGE_2$ or its active analogue could be administered as 0.0001-10 micro Molar to patients immediately prior to and daily after receiving a hematopoietic graft.

$PGE_2$ treatment in vitro results in an increase in the proportion of SKL cells actively in cell cycle within 24 hours post-treatment. In addition, transplantation of $PGE_2$-treated cells in BrdU treated recipient mice showed ~2-fold more donor SKL cells in $S+G_2/M$ phase of the cell cycle compared to transplanted cells pulsed with vehicle only.

Survivin is thought to be required for HSPC to enter and progress through cell cycle and Survivin's deletion in conditional knockout mice indicates it is required for HSPC maintenance. Studies reported herein found elevated mRNA and protein levels of Survivin, with concomitant reduced active caspase-3, a protease that mediates apoptosis, in $PGE_2$-treated SKL cells. Survival assays indicated that $PGE_2$ dose-dependently decreased apoptosis of SKL cells in vitro, coincident with a 1.7 fold increase in Survivin protein expression and a decrease in active caspase-3 (23-59% decrease; 24-72 hours post exposure).

It is likely that enhanced HSPC survival, mediated through Survivin, contributes to enhanced engraftment. Pulse exposure to $PGE_2$ increases the proportion of HSPC in cell cycle by ~2-fold, with increased frequency of HSPC, CRU and homing of BrdU+ SKL cells and maintenance of enhanced HSPC frequency in primary and secondary transplants. One non-limiting explanation of these results is that $PGE_2$ pulse-exposure may initiate a single round of HSPC self-renewal. For example, EP2 and EP4 receptor activation is associated with phosphorylation of glycogen synthase kinase-3 (GSK-3) and increased β-catenin signalling (Hull et al., 2004; Regan, 2003), which is downstream of the Wnt pathway, which has been implicated in HSPC survival and self-renewal (Fleming et al, 2008; Khan and Bendall, 2006). Signalling by $PGE_2$ possibly through EP4 but not limited exclusively to EP4 might directly increase β-catenin. Synergistic cross-talk between COX-2 and Wnt pathways has been suggested (Wang et al, 2004).

Survivin also facilitates HSPC cell cycling through $p21^{WAF1/CDKN1}$ (Fukuda et al, 2004), known to be involved in HSPC function (Cheng et al, 2000), and blocks caspase-3 activity (Li et al, 1998; Tamm et al, 1998). Recently, p21 was implicated in HSPC self-renewal (Janzen et al, 2008). One finding drawn from the studies reported herein is that PGE2 up-regulates Survivin and decreases caspase-3 suggesting that the Survivin pathway may be involved in the effects of $PGE_2$ on increased self-renewal. It is also interesting to note that Survivin (Peng et al., 2006) and CXCR4 (Staller et al, 2003; Zagzag et al, 2005) transcription are up-regulated by the transcription factor hypoxia-inducible factor-1 alpha (HIF-1 alpha), which can be stabilized by $PGE_2$ (Liu et al, 2002; Piccoli et al, 2007), possibly linking some $PGE_2$ responsive pathways with cell survival, homing, and proliferation/self-renewal of HSPC.

These studies suggest that the ~4-fold increase in HSPC frequency observed after $PGE_2$ treatment results from a ~2-fold or more homing of HSPC to recipient marrow with a ~2-fold more HSPC undergoing self-renewal. These results may help to define novel mechanisms of action whereby $PGE_2$ enhances HSPC function and they suggest unexpected therapeutic approach for facilitating hematopoietic transplantation, particularly for hematopoietic grafts in which a limiting number of cells results in a poor potential for engraftment.

One aspect disclosed herein is a method for enhancing the viral transduction efficacy in stem cell gene therapy. The ex vivo $PGE_2$ treatment of stem cells increased the self-renewal division and survival of such cells, which is an important factor for successful viral vector mediated gene integration. $PGE_2$ promoted stem cell self-renewal division/survival can be incorporated in current stem cell transduction protocols, thus increasing the overall gene transduction efficacy in stem cell gene therapy.

Reported herein are some methods of using $PGE_2$ to enhance HSPC engraftment, a multistep process that includes the mobilization of donor cells, the maintenance of HSPCs and the homing of HSPC in the recipient body. Under some conditions these methods result in a 4-fold increase in HSPC frequency and engraftment results possibly, for example, from the cumulative effect of a 2-fold increase in HSPC homing and a 2-fold increase in HSPC cell cycle activity under the direct influence of $PGE_2$. Although the precise signaling pathways are yet to be determined, one non-limiting explanation for this effect is that enhanced engraftment is due to up-regulation of factors such as CXCR4 and Survivin.

The ability of $PGE_2$ to improve the homing and the survival and/or proliferation of HSPC may be clinically significant, especially in settings in which HSPC numbers are limiting, e.g. UCB and some mobilized PB products, or for viral gene transduction in stem cell gene therapy. Our limiting dilution transplant studies illustrate that equivalent engraftment results can be achieved with one-fourth the number of $PGE_2$-treated cells compared to controls that are not so treated. These results demonstrate the utility of using $PGE_2$ under conditions in which HSPC numbers are limiting. While all four EP receptor subtypes appear to be expressed on HSPC, it is not clear which of these receptors (or if all of them) are involved in the engraftment function. It is consistent with these results that enhanced engraftment/recovery can be achieved by administering $PGE_2$ in vivo or if $PGE_2$ used in vivo can further facilitate engraftment of HSPC exposed to $PGE_2$ ex vivo.

Materials and Methods

Materials

Mice C57B1/6 mice were purchased from Jackson Laboratories (Bar Harbor, Me., USA). B6.SJL-PtrcAPep3B/BoyJ (BOYJ) and F1 C57B1/6/BOYJ hybrids were bred in-house. All animals were housed in micro-isolator cages with continuous access to food and acidified water. Mice used in transplant studies received Doxycycline feed at time of radiation and for 30 days post-transplant. The Animal Care and Use Committee of Indiana University School of Medicine approved all animal protocols.

Flow Cytometry All antibodies were purchased from BD Biosciences unless otherwise noted. For detection and sorting of murine KL and SKL cells, streptavidin conjugated with PE-Cy7 (to stain for biotinylated MACS lineage antibodies (Miltenyi Biotech, Auburn, Calif.)), c-kit-APC, Sca-1-PE or APC-Cy7, CD45. 1-PE and CD45.2-FITC were used. UCB CD34$^+$ cells were detected using anti-human-CD34-APC. For multilineage analysis, APC-Cy7-Mac-1, PE-Cy7-B-220 and APC-CD3 were used. EP receptors were detected with anti EP1, EP2, EP3 and EP4 rabbit IgG (Cayman Chemicals) and secondary staining with FITC-goat-anti-rabbit IgG (Southern Biotech, Birmingham, Ala.). CXCR4 expression was analyzed using streptavidin-PECy7, c-kit-APC, Sca-1-APC-Cy7, and CXCR4-PE. Apoptosis was measured with FITC-Annexin-V. For Survivin and active caspase-3 detection, cells were permeabilized and fixed using the CytoFix/CytoPerm kit (BD) and stained with anti-active-caspase-3-FITC Flow Kit (BD) or Survivin-PE (R&D Systems).

For cell cycle analysis, cells were stained with 7AAD or the FITC-BrdU Flow Kit (BD). All analyses were performed on a LSRII and sorting was performed either a FACSAria or FACSVantage sorter (BD). Cell Quest Pro and Diva software (BD) were used for data acquisition and analysis.

Methods

Limiting Dilution Competitive and Non-Competitive Transplantation

WBM cells (CD45.2) were treated on ice for 2 hours with either 1 microMolar dmPGE$_2$ (Cayman Chemical, Ann Arbor, Mich.) per 1×10$^6$ cells or 0.01% ETOH in sterile, non-pyrogenic PBS. After incubation, cells were washed twice and mixed with 2×10$^5$ congenic CD45.1 competitor marrow cells at ratios of 0.075:1, 0.25:1, 1:1, and 2.5:1 and transplanted into lethally irradiated CD45.1 mice (1100-cGy split dose) by tail-vein injection (5 mice per dilution). CD45.1 and CD45.2 cells in PB were determined monthly by flow cytometry. For head-to-head competitive transplants, WBM from CD45.1 mice and CD45.2 mice were treated with vehicle or dmPGE$_2$ and mixed with 2×10$^5$ competitor marrow cells from CD45.1/CD45.2 mice at ratios of 0.075:1, 0.25:1, 1:1, and 2.5:1 and transplanted into lethally irradiated CD45.1/CD45.2 mice. The proportion of CD45.1, CD45.2, and CD45.1/CD45.2 cells in PB was determined monthly. HSPC frequency was quantitated by Poisson statistics using L-CALC software (Stem Cell Technologies, Vancouver BC, Canada) with <5% contribution to chimerism considered a negative recipient. Competitive repopulating units (CRU) were calculated as described (Harrison, 1980). For secondary transplants, 2×10$^6$ WBM from previously transplanted F1 Hybrid mice at the 1:1 ratio at 20 weeks post-transplant were injected into lethally irradiated F1 Hybrid mice in non-competitive fashion and PB chimerism and tri-lineage reconstitution evaluated monthly.

Analysis of HSPC homing to bone marrow in vivo CD45.2 WBM was labeled with CFSE (Molecular Probes, Eugene, Ore.) washed and treated on ice with either 1 microMolar dmPGE$_2$ or vehicle. After treatment, cells were washed and 2×10$^7$ cells transplanted into lethally irradiated CD45.2 mice. After 16 hours, femurs and tibias were flushed, and a proportion of mouse marrow Lin$^r$ cells depleted using MACS microbeads (Miltenyi Biotech), stained with fluorochrome-conjugated-antibodies specific for biotin (lineage), c-kit (K), and Sca-1 (S) and the total number Of CFSE$^+$ WBM (non lineage depleted), KL and SKL cells determined. For congenic homing studies, Lin$^{neg}$ CD45.1 cells were treated on ice with 1 microMolar dmPGE2, vehicle, or PBS. After incubation, cells were washed and 2×10$^6$ cells transplanted into CD45.2 mice. After 16 hours, recipient bone marrow was harvested, lineage depleted, stained, and donor CD45.1 SKL cells determined. For competitive, head-to-head homing studies using sorted SKL cells, Lin$^{neg}$ cells from CD45.2 and CD45.1 mice were FACS sorted, cells treated with either dmPGE2 or vehicle for 2 hours, washed and 3×10$^4$ CD45.1 (vehicle or dmPGE2 treated) plus 3×10$^4$ CD45.2 (dmPGE$_2$ or vehicle treated) SKL cells transplanted into lethally irradiated F1 Hybrid mice. To evaluate the role of CXCR4 in homing studies, Lin$^{neg}$ CD45.2 cells were treated on ice with vehicle or 1 microMolar dmPGE2 plus 10 microMolar AMD3100 (AnorMed Inc., Vancouver, BC, Canada) and 2×10$^6$ treated cells injected into lethally irradiated CD45.1 mice. Homed SKL cells were analyzed 16 hours post-transplant.

Expression of EP receptors, CXCR4 and Survivin Replicate Lin$^{neg}$ cell samples from CD45.2 mice were stained for SKL and each of the EP receptors and surface receptor expression on KL and SKL cells determined by FACS. For human EP receptors, UCB was obtained from Wishard Hospital, Indianapolis, Ind. with Institutional Review Board approval. Mononuclear cells were isolated on Ficoll-Paque™ Plus (Amersham Biosciences) and CD34$^+$ cells positively selected with MACS microbeads (Miltenyi Biotech) (Fukuda and Pelus, 2001). Replicate cells were stained for CD34 and each of EP receptors and surface expression determined by FACS. To evaluate CXCR4, Survivin and active caspase-3, Lin$^{neg}$ cells or CD34$^+$ UCB were treated on ice with either 1 micrMolar dmPGE2 or vehicle control for 2 hours, washed, and then cultured in RPMI-1640+ 10% FBS at 37° C. for 24 hours. Cells were stained for SKL (murine cells) and CXCR4, Survivin, and/or active caspase-3, as described above, and analyzed by FACS.

Cell Cycle Analysis For in vitro cell cycle analysis, Lin$^{neg}$ cells were treated with either 1 microMolar dmPGE$_2$ or vehicle for 2 hours, washed, and cultured in Stem Cell Pro Media (Stem Cell Technologies) with rmSCF (50 ng/ml) (R&D Systems, Minneapolis, Minn.), rhFlt-3 and rhTPO (100 ng/ml each) (Immunex, Seattle, Wash.). After 20 hours, cells were stained for SKL, fixed and permeabilized, and stained with 7AAD (BD Biosciences, San Jose, Calif.). The proportion of SKL cells in S+G2/M phase was determined by measuring DNA content by FACS. For in vivo cell cycle analysis, CD45.2 mice were lethally irradiated and transplanted with 5×10$^6$ Lin$^{neg}$ cells from CD45.1 mice treated with either 1 microMolar dmPGE$_2$ or vehicle for 2 hours. At the time of transplant, recipient mice received 1 milligram/mL BrdU (Sigma Aldrich, St. Louis, Mo.) in drinking water and 1 mg per mouse BrdU LP. After 16 hours, recipient marrow was isolated, lineage depleted, and stained for CD45.1, SKL and BrdU. The proportion of homed (CD45.1$^+$) SKL cells that were BrdU$^+$ was determined by FACS in individual mice.

Apoptosis Assay Lin$^{neg}$ cells were treated on ice with 0.1 nanoMolar to 1 microMolar dmPGE2 or vehicle control, washed and incubated in RPMI-1640+2% FBS, without growth factors at 37° C. to induce apoptosis. After 24 hours, cells were stained for SKL and Annexin-V and the proportion of Annexin-V$^+$ SKL cells was determined by FACS.

Reverse Transcription and QRT-PCR Total RNA was obtained using the absolutely RNA purification kit (Stratagene, La Jolla, Calif.). A constant amount of RNA was reverse transcribed with random primers (Promega, Madison, Wis.) and MMLV-reverse transcriptase (Promega) in a volume of 50 micro Liter with 1 milliMolar dNTPs and RNase inhibitor as described (Fukuda and Pelus, 2001). DNase and RNase free water (Ambion, Austin, TX) was added to obtain a final concentration equivalent of 10 nanogram RNA/microLiter and 5 microLiter used for QRT- PCR. Primers for SYBR Green QRTPCR were designed to produce an amplicon size of 75-150 bp. QRT-PCR was performed in a total volume of 30 microLiter using Platinum SYBR Green qPCR supermix UDG with Rox (Invitrogen, Carlsbad, Calif.) in an ABI-7000 (Applied Biosystems, Carlsbad, CA), with an activation step of 50° C. for 2 min, denaturation at 95° C. for 2 min and amplification for 45 cycles at 95° C.-15 sec, 50° C.-30 sec, 72° C.-30 sec, followed by dissociation to confirm that only one product was obtained.

Nonsteroidal anti-inflammatory compounds that can be used to practice some aspects of the invention, include, but are not limited to, compounds such as: Celecoxib (4-[5-(4-methylphenyl)-3-(trifluoromethyl) pyrazol-1-yl]benzenesulfonamide) sold under the trade name Celebrex®; Rofecoxib (4-(4-methylsulfonylphenyl)-3-phenyl-5H-furan-2-one) sold under the trade name Vioxx®; Aspirin (2-acetoxybenzoic acid); Etoricoxib (5-chloro-6'-methyl-3-[4-(methylsulfonyl)phenyl]-2,3'-bipyridine); Valdecoxib (4-(5-methyl-3-phenylisoxazol-4-yl) benzenesulfonamide) sold under the trade name BEXTRA®; Ibuprofen ((&S)-2-(4-isobutylphenyl) propanoic acid); Naproxen ((+)-(S)-2-(6-methoxynaphthalen-2-yl) propanoic acid); Diclofenac (2-(2-(2,6-dichlorophenylamino)phenyl)acetic acid) marketed under the trade name VOLTAREN®; Licofelone ([6-(4-chlorophenyl)-2,2-dimethoyl-7-phenyl-2,3-dihydro-1H-pyrrolizin-5-yl]acetic acid); Indomethacin (2-{1-[(4-chlorophenyl)carbonyl]-5-methoxy-2-methyl-1H-indol-3-yl}acetic acid) meloxicam ((8E)-8-[hydroxy-[(5-methyl-1,3-thiazol-2-yl)amino]methylidene]-9-methyl-10,10-dioxo-10$\lambda^6$-thia-9-azabicyclo[4.4.0]deca-1,3,5-trien-7-one) sold under the trade name Metacam; Etodolac (2-(1,8-Diethyl-4,9-dihydro-3H-pyrano[3,4-b]indol-1-yl)acetic acid); ketorolac ((±)-5-benzoyl-2,3-dihydro-1H-pyrrolizine-1-carboxylic acid, 2-amino-2-(hydroxymethyl)-1,3-propanediol) marketed under the trade name Toradol.

Compounds that act as antagonists to at least one $PGE_2$ receptor include, but are not limited to, compounds available from Cayman Chemical Company (Ann Arbor, Mich., U.S.A.) or other lists maintained/sold by chemical supply companies.

Statistical Analysis All pooled values are expressed as Mean±SEM. Statistical differences were determined using the paired or unpaired two-tailed t-test function in Microsoft Excel (Microsoft Corp, Seattle, Wash.) as appropriate. As used herein, especially in some of the figures, the terms, 'dmPGE$_2$' and 'dmPGE' are used interchangeably.

EXAMPLES

1. PGE$_2$ Increases Long-Term Repopulating HSPC Frequency and Engraftment

Figure 1A:
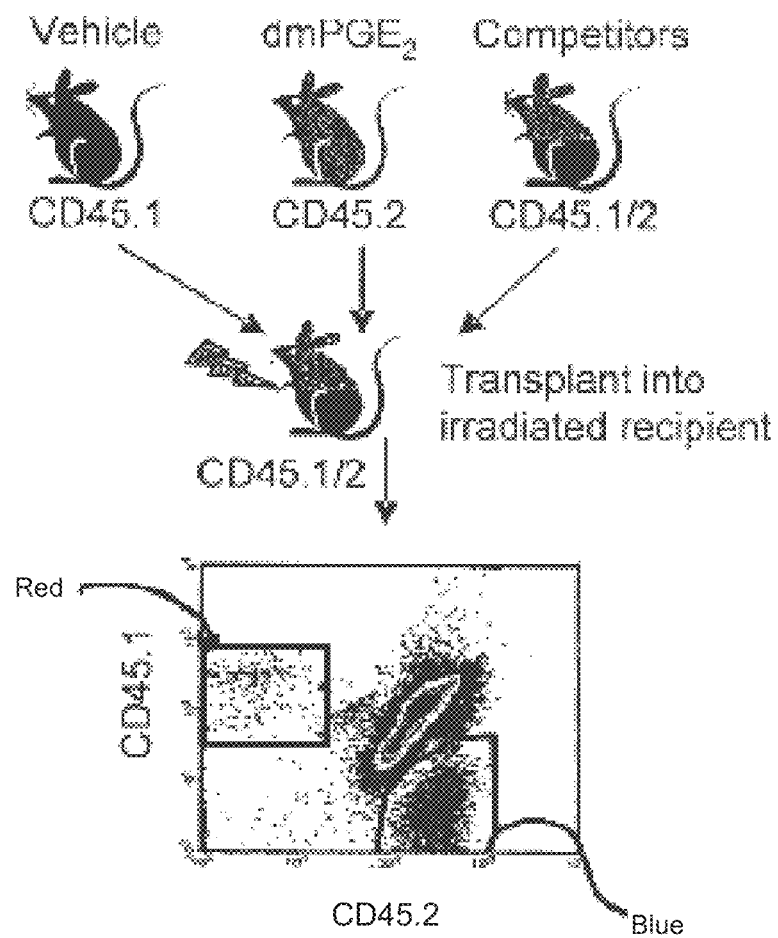
FIG. 1A. Outline of an experiment to test the effect of PGE2 enhances hematopoietic stem cell engraftment (upper panel); a representative flow plot illustrating the populations of CD45.1 and CD45.2 cells (lower panel).

Using a limiting dilution competitive transplant model utilizing CD45.2 and CD45.1 congenic grafts transplanted into CD45.1/CD45.2 hybrid mice, demonstrated that short-term exposure of HSPC to PGE2 produces long-term enhancement of HSPC and competitive repopulating unit (CRU) frequency. Referring now to FIG. 1A, bone marrow from CD45.1 or CD45.2 mice were treated with vehicle or dmPGE2 respectively. CD45.1/CD45.2 hybrid marrow cells were used as competitors. Limiting dilutions were transplanted into lethally irradiated (1100 cGys, split dose) CD45.1/CD45.2 hybrid mice and chimerism in PB analyzed for 20 weeks. A representative flow plot detecting each cell population is shown (bottom panel).

Figure 1B:
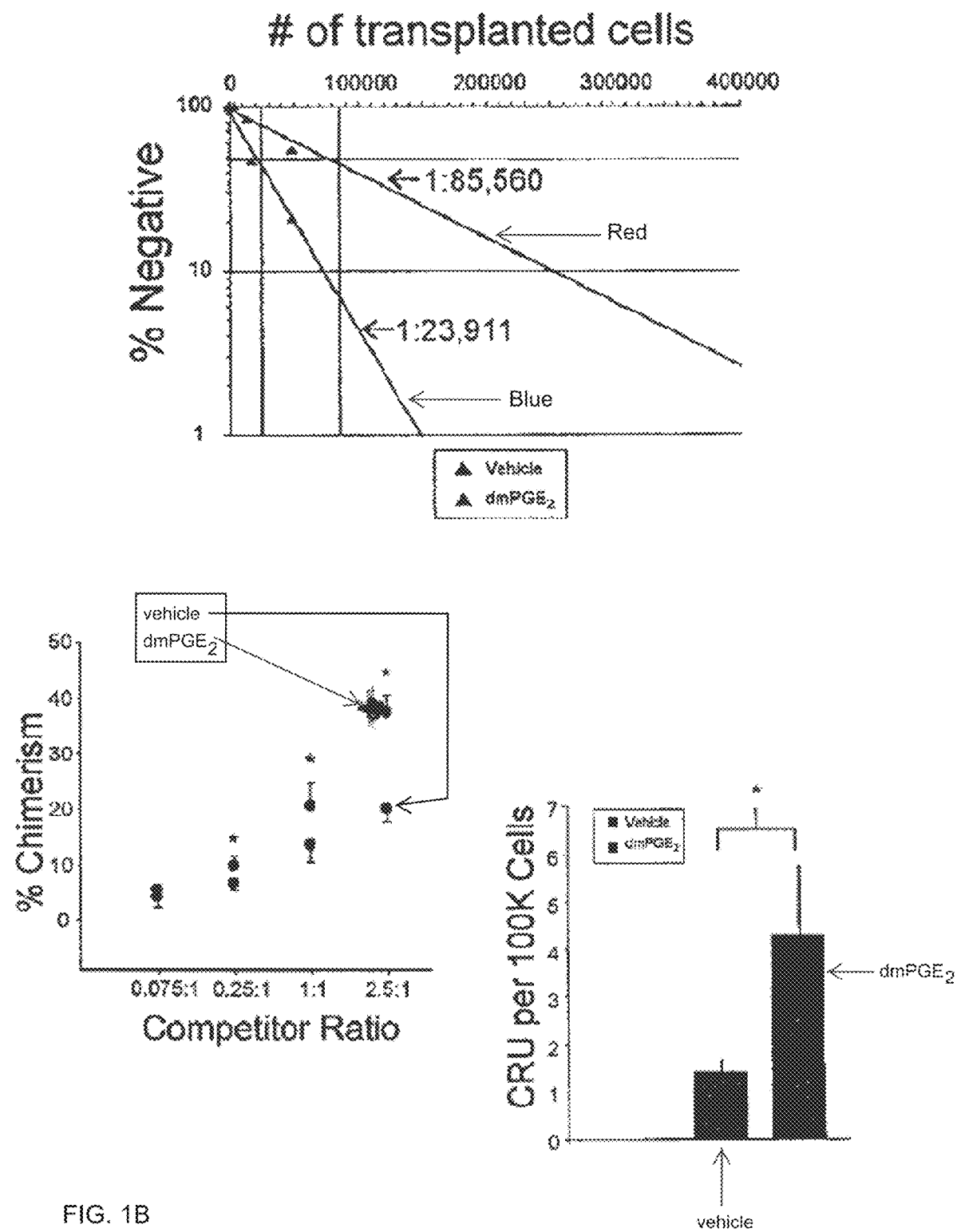
FIG. 1B. Graph of percent negative cells versus number of transplanted cells (upper panel); Scatter graph of percent chimerism versus competitor ratio (lower conditions (lower right panel).

Referring now to FIG. 1B, frequency analysis (top) for vehicle (red) or dmPGE$_2$ (blue) pulsed cells, determined by Poisson statistics, at 12 weeks; Po=85,560 (vehicle) and Po=23,911 (dmPGE$_2$ treated). Chimerism in PB and CRU analysis is shown at 12 weeks (Mean±SEM). Data represent 2 pooled experiments, n=5 mice/group/expt, each assayed individually.

Referring now to FIG. 1C, HSPC frequency analysis in recipients of vehicle or PGE$_2$-treated bone marrow over 20 weeks. Fold change indicates increase in frequency of engraftment of dmPGE2-pulsed cells compared to vehicle.

Figure 1D:
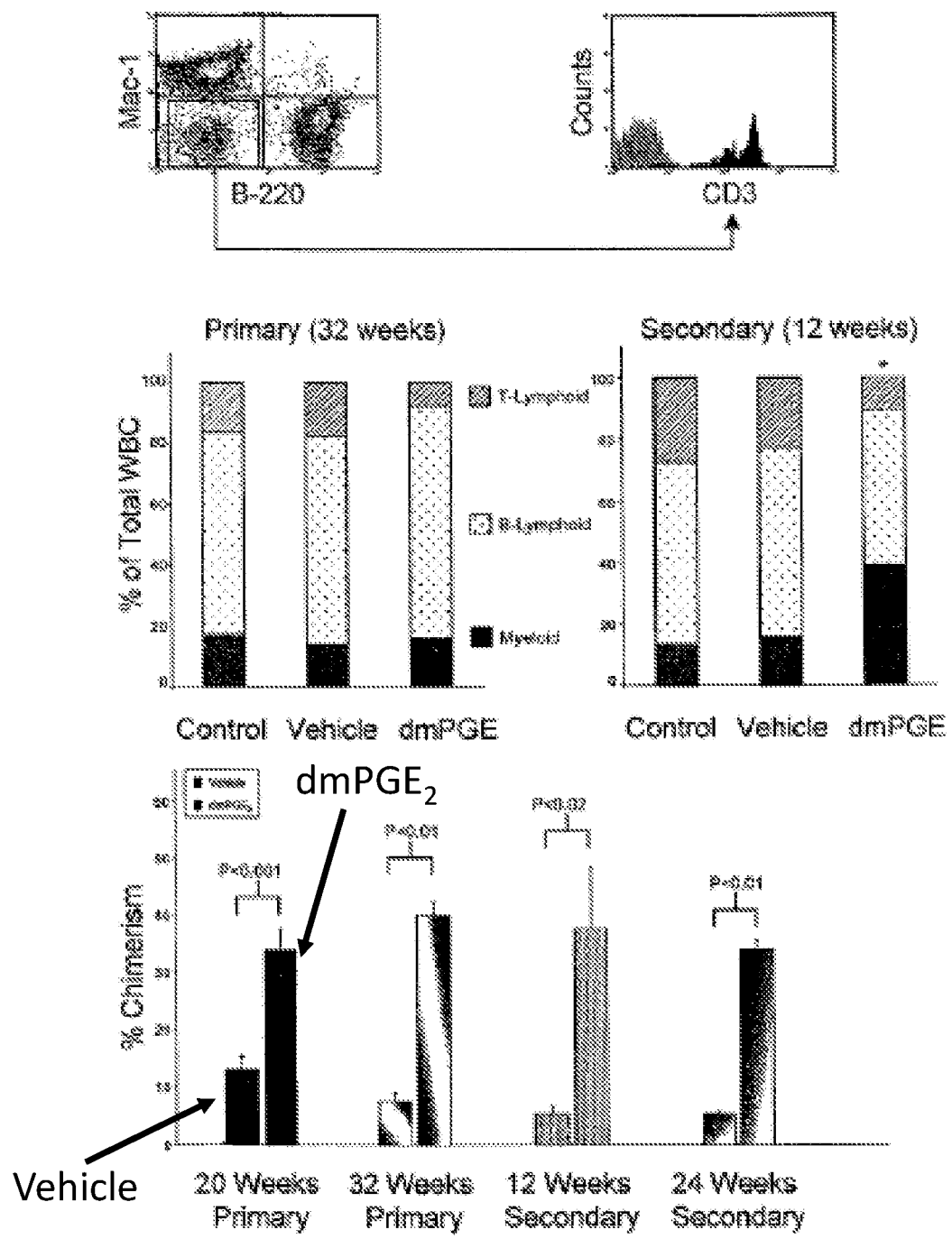
FIG. 1C. Table summarizing Repopulating Cell Frequency plotted over 20 weeks for cells treated with and without dmPGE2.

Referring now to FIG. 1D, representative FACS plots of multi-lineage reconstitution (myeloid, B and T-lymphoid). Referring now to FIG. 1D, middle panels multi-lineage analysis for primary transplant (32 weeks left panel) and a cohort of 4 mice that received transplants from primary transplanted mice at 20 weeks, with analysis 12 weeks later (right panel). Increased chimerism of dmPGE$_2$ treated cells vs. vehicle is shown for primary transplant at 20 weeks (time of secondary transplant) and secondary transplant 12 weeks later (bottom panel). Data for 20 week primary transplant were from 2 pooled experiments, n=5 mice/group/expt, each assayed individually. Data for 12 week secondary transplant, n=4 mice/group, each assayed individually.

Still referring to FIG. 1D, serial transplantation assesses self-renewal and expansion of HSPC in transplanted hematopoietic grafts. To investigate the expansion of long-term repopulating cells (LTRC) exposed to dmPGE$_2$ and vehicle ex vivo, marrow was harvested from primary transplanted animals at 20 weeks post-transplant and transplanted into secondary recipients. Analyziz of PB 12 weeks after secondary transplant showed multilineage reconstitution by cells from all transplanted mice, indicative of self-renewal of primary transplanted LTRC. The increase in chimerism resulting from dmPGE$_2$ exposure seen in primary donors was also seen in secondary transplants without any additional treatments. In addition, a trend towards increased competitiveness of HSPC previously treated with dmPGE$_2$ was observed in secondary transplants, with a slight bias towards myeloid lineage reconstitution.

This model permits quantitative comparison of engraftment and competitiveness of HSPC from control and dmPGE$_2$ treatment groups within the same animal (FIG. 1A), as well as endogenous repopulation of host cells. At 12 weeks post-transplant, analysis of peripheral blood (PB) showed increased chimerism of dmPGE2-treated cells compared to vehicle treated cells, with ~4-fold increase in HSPC frequency and competitive repopulating units (CRU), recognized measures of long-term-repopulating capacity (FIG. 1B). Throughout 20 weeks of follow up post-transplant, an ~4-fold increase in HSPC frequency was maintained, indicating that the effect of dmPGE$_2$ pulse exposure was stable (FIG. 1C). At 32 weeks post-transplant, reconstitution was seen for B- and T-lymphoid and myeloid lineages in PB, with no discernible differences between untreated competitor cells, dmPGE$_2$ or vehicle treated cells (FIG. 1D).

2. Murine and Human Hematopoietic Stem and Progenitor Cells (HSPC) Express PGE2 Receptors.

Reportedly, PGE$_2$ interacts with 4 specific, highly conserved G-protein coupled receptors; EP1-EP4 (Sugimoto and Narumiya, 2007; Tsuboi et al, 2002). EP receptor repertoire accounts for multiple, sometimes opposing responses attributed to PGE$_2$ (Breyer et al, 2001). PGE2 receptor subtype expression on HSPC is not known previously. Referring now to FIG. 2A, analysis of EP receptors on c-kit$^+$ Lin$^{neg}$ (KL) cells, enriched for hematopoietic progenitor cells (HPC), and Sca-1$^+$ c-kit$^+$ Lin$^{neg}$ (SKL) cells, enriched for HSPC, showed that all four EP receptors (EP3+, EP2, EP1 and EP4) were expressed. Referring now to FIG.

2A, (right panel) in addition, QRT-PCR detected mRNA for all four EP receptors in FACS sorted KL and SKL cells. Referring now to FIG. 2A, (middle panel) dissociation curves for EP3 showed several peaks, consistent with the known multiple splice variants of EP3 (Namba et at, 1993). No significant quantitative differences in surface expression or mRNA levels between any of the EP receptor subtypes was seen for KL or SKL cells. Referring now to FIG. 2B, (right panel) analogous to murine cells, all four receptor subtypes were expressed on the surface of human $CD34^+$ UCB cells and QRT-PCR analysis detected mRNA for all four EP receptors (FIG. 2B).

3. Short-Term $PGE_2$ Exposure Increases HSPC Homing Efficiency

Enhanced HSPC engraftment observed upon pulse-exposure to $PGE_2$ may result from increased HSPC number and/or cell cycle status effects on facilitating cells or effects on HSPC homing or proliferation in the host marrow. Irrespective of its cause a marrow niche is required for HSPC to self-renew and differentiate and it is very likely that only HSPC homing to these niches can provide long-term repopulation. Referring now to FIG. 3A, in order to assess HSPC homing, CFSE labeled whole bone marrow (WBM) CD45.2 cells were pulsed with $dmPGE_2$ or vehicle for 2 hours on ice, washed and injected IV in lethally irradiated CD45.2 hosts. After 16 hours, total $CFSE^+$ cells homing to bone marrow as well as the number of homed events within the KL and SKL cell populations were quantified. No difference in the percentage of $CFSE^+$ cells homing to the marrow was observed between $dmPGE_2$ and vehicle-treated cells when total WBM cells were evaluated; however, significantly more SKL cells homed to the marrow than to the control. Referring now to FIG. 3B, in a congenic model, a significantly greater percentage of SKL cells was also observed for $dmPGE_2$-treated cells compared to vehicle-treated or un-manipulated cells. No difference in homing efficiency was seen between untreated and vehicle-treated cells.

Referring now to FIG. 3C, in order to determine whether the enhancing effect of $dmPGE_2$ on SKL cell homing was direct or indirect, the homing of enriched HSPC in a head-to-head transplant model was compared with other cells. Highly purified SKL cells from both CD45.2 and CD45.1 mice were isolated by FACS sorting, treated with $dmPGE_2$ or vehicle, and $3\times10^4$ vehicle-treated CD45.1 cells plus $3\times10^4$ $dmPGE_2$-treated CD45.2 cells transplanted into CD45.1/CD45.2 mice. An additional cohort was concurrently transplanted with congenic strain and treatment groups were switched to test for any bias in strain homing. Similar to studies using WBM, $dmPGE_2$ pulse-exposure of purified SKL cells increased their homing efficiency by 2-fold, strongly suggesting a direct effect of $PGE_2$ on HSPC. Although SKL cells are not a homogenous HSPC population, they are highly enriched for LTRC (Okada et al, 1992; Spangrude and Scollay, 1990). 4. $PGE_2$ increases HSPC CXCR4, and the CXCR4 antagonist AMD3100 blocks enhanced homing Referring now to FIG. 4A, the stromal-cell-derived factor-1 alpha (SDF-1a)/CXCR4 axis has been implicated in HSPC trafficking and homing. The study evaluated whether the improved homing of $dmPGE_2$-treated HSPC was the result of increased SDF-1a/CXCR4 signaling. Pulse-exposure of $Lin^{neg}$ cells to $dmPGE_2$ increased CXCR4 expression on KL and SKL cells (FIG. 4A); similarly, $dmPGE_2$ pulse exposure increased CXCR4 expression on $CD34^+$ UCB cells as expected. QRT-PCR demonstrated elevated CXCR4 mRNA levels in $dmPGE_2$-treated cells compared to vehicle, with maximal elevation observed at 6 hours (data not shown).

Referring now to FIG. 4B, in order to determine if up-regulated CXCR4 played a role in the enhanced homing observed after $PGE_2$ treatment, the selective CXCR4 antagonist AMD3100, which inhibits in vitro migration to SDF-1 and homing of HSPC in vivo was used. $PGE_2$ pulse-exposure increased homing of SKL cells by ~2-fold, and incubation of vehicle or $dmPGE_2$-pulsed cells with AMD3100 reduced SKL cell homing and abrogated the improved homing efficiency of $dmPGE_2$-pulsed cells.

5. $PGE_2$ Decreases HSPC Apoptosis Coincident with an Increase in Survivin.

$PGE_2$ treatment produced a 4-fold increase in HSPC frequency and CRU (FIG. 1), but only a 2-fold enhancement in homing (FIG. 3), suggesting that other events are involved in enhanced engraftment. Apoptosis is an important regulatory process in normal and malignant hematopoiesis and $PGE_2$ has been implicated in anti-apoptotic signalling. Moreover, activation of cAMP, a downstream signaling molecule of EP receptors, inhibits apoptosis in $CD34^+$ cells. One hypothesize consistent with these results is that $dmPGE_2$ treatment affects survival and/or proliferation of HSPC, which contributes to enhanced engraftment. To evaluate an effect of $dmPGE_2$ on HSPC survival, $Lin^{neg}$ cells were pulsed with 0.1 nanoMolar-1 microMolar $dmPGE_2$ or vehicle and cultured in serum-reduced culture medium without growth factors. Pulse-exposure to $dmPGE_2$ reduced apoptosis in SKL cells in a dose dependent fashion (FIG. 5A), reaching ~65% inhibition at 1 microMolar.

The inhibitor of apoptosis protein survivin is an important regulator of apoptosis and proliferation in both normal and malignant hematopoietic cells. Referring now to FIG. 5B, these results demonstrate that $PGE_2$ affected Survivin in HSPC. At 24 hours post-$dmPGE_2$-pulse, intracellular Survivin levels were significantly higher in both murine SKL cells and $CD34^+$ UCB cells (1.7 and 2.4 fold, respectively) compared to control and QRT-PCR analysis indicated elevated Survivin mRNA compared to control.

Referring now to FIG. 5C decreased active caspase-3 coincident with an increase in Survivin was seen at 24, 48, and 72 hours post-exposure of SKL cells to $dmPGE_2$ compared to control.

6. $PGE_2$ Treatment Increases HSPC Proliferation

Survivin regulates HSPC entry into and progression through cell cycle. Furthermore, β-catenin, implicated in HSPC proliferation and self-renewal, lies downstream of EP receptor pathways. The ability of $PGE_2$ to modulate these cell cycle regulators suggests that an increase in HSPC self-renewal and proliferation might contribute to the enhanced engraftment of $dmPGE_2$-pulsed cells. To test this hypothesis, the cell cycle status of SKL cells pulsed with $dmPGE_2$ or vehicle in vitro was analyzed. Referring now to FIG. 6A, pulse-exposure to $dmPGE_2$ increased DNA content in SKL cells, an indication of increased cell cycling (left panels, upper right quadrant). In 3 experiments, 60% more SKL cells were in S+G2/M phase of the cell cycle after $dmPGE_2$ treatment compared to controls (FIG. 6A right panel). No significant effect on cell cycle rate of KL or $Lin^{neg}$ cells was seen (not shown); suggesting that $dmPGE_2$ selectively increases the cycling state of early HSPC.

To confirm the effect of $dmPGE_2$ on enhancement of HSPC cell cycle observed in vitro, marrow cells were pulsed with $dmPGE_2$ and injected into congenic mice treated with BrdU post-transplant, and the proportion of donor $BrdU^+$ SKL cells was determined 16 hours later. Referring now to FIG. 6B, ~2-fold increase in the proportion of homed SKL cells in S+G2/M phase was observed for cells pulsed with dmPGE$_2$ prior to transplant, confirming that short-term exposure of HSPC to dmPGE$_2$ stimulates HSPC to enter and progress through cell cycle in vivo.

7. Inhibition of Endogenous PGE$_2$ Biosynthesis by the Dual COX1/COX2 Inhibitor Indomethacin Mobilizes HSPC.

Since PGE$_2$ increases CXCR4 receptor expression and SDF-1/CXCR4 signalling is important for trafficking and retention of HSPC in the marrow. One hypothesis consistent with these results is that inhibition of endogenous PGE$_2$ biosynthesis by the dual COX1/COX2 inhibitor indomethacin would also mobilize HSPC. Referring to FIGS. 7A & 7B, it shows effects of daily SC administration of 150 μg/kg indomethacin or 150 ug/kg baicalein alone (FIG. 7A) or with G-CSF (FIG. 7B) for 4 days on CFU-GM mobilization. Referring now to FIG. 7A, administration of 150 μg/kg indomethacin, SC, once daily for 4 days, produced a 4-fold increase in the number of mobilized progenitor cells. Referring now to FIG. 7B, Coadministration of indomethacin with G-CSF produced a highly synergistic increase in peripheral blood stem cell mobilization. The lipoxygenase inhibitor baicalein had no effect on baseline or G-CSF-induced CFU-GM mobilization, suggesting that the observed effects were specific to inhibition of the cyclooxygenase pathway. Data are expressed as mean±SEM CFU-GM mobilized per ml of blood for N=3 mice each assayed individually.

8. Pulse Exposure of Murine and Human HSPC to PGE$_2$ Increases CXCR4 Expression.

To evaluate CXCR4, Lineage$^{neg}$ mouse bone marrow cells or CD34$^+$ UCB were treated on ice with either 1 microMolar dmPGE$_2$ or vehicle control for 2 hours, washed, and then cultured in RPMI-1640/10% HI-FBS at 37° C. for 24 hours, stained for SKL (murine cells) or CD34 (human) and CXCR4 and analyzed by FACS.

Referring now to FIG. 4A, CXCR4 expression on murine KL and SKL cells and human CD34$^+$ UCB cells 24 hours after treatment with dmPGE$_2$. Data are expressed as Mean±SEM % change in mean fluorescence intensity (MFI) of CXCR4 due to treatment with dmPGE$_2$ or vehicle (n=3). Analysis by QRT-PCR demonstrates a 2.65 fold increase in CXCR4 mRNA.

9. Pulse Exposure of Murine SKL Cells to PGE$_2$ Increases Migration to SDF-1a.

Freshly isolated Lineage$^{neg}$ mouse bone marrow cells were pulsed with dmPGE$_2$ or vehicle for 2 hours, washed and resuspended in media with 10% HI-FCS and cultured at 37° C. for 16 hours. After incubation, cells were washed, resuspended in RPMI/0.5% BSA and allowed to migrate in transwells to rmSDF-1a for 4 hours. Total cell migration was measured by flow cytometry. Referring now to FIG. 9, total SKL cell migration was higher for cells pulsed with dmPGE$_2$. Data are the Mean±SEM percent migration for 3 experiments. $‡P<0.05$ for dmPGE$_2$ treated cells compared to cells treated with vehicle.

10. Pulse Exposure of Human CD34$^+$ cells to PGE$_2$ Increases Migration to SDF-1a.

Freshly isolated UCB CD34$^+$ cells were pulsed with dmPGE$_2$ or vehicle for 2 hours, washed and resuspended in media with 10% HI-FCS and cultured at 37° C. for 16 hours. After incubation, cells were washed, resuspended in RPMI/0.5% BSA and migration to rhSDF-1 measured by flow cytometry. To block the CXCR4 receptor, replicate cells were incubated with 5 micrograms/ml AMD3100 for 30 minutes prior to the migration assay. Referring now to FIG. 10, the data are the Mean±SEM percentage migration for 3 experiments.

11. Blocking the CXCR4 Receptor Blocks PGE$_2$ Enhancement of SKL Cell Homing.

To evaluate the role of CXCR4 in homing, Lineage CD45.2 cells were treated with vehicle or 1 microMolar dmPGE$_2$ plus 10 microMolar AMD3100, 2×10$^6$ treated cells injected into lethally-irradiated CD45.1 mice and homed SKL cells recovered 16 hours post-transplant and analyzed by FACS. Referring now to FIG. 11. homing efficiency of vehicle and dmPGE$_2$ treated cells to bone marrow in the absence and presence of 10 microMolar AMD3100. Cells were incubated with AMD3100 for 30 minutes prior to the homing assay.

12. PGE$_2$ Increases the Cell Cycle Rate of Murine SKL Cells In Vitro.

Lineage$^{neg}$ cells were treated with either vehicle or 1 microMolar dmPGE$_2$ for 2 hours, washed and cultured in media with rmSCF, rhFlt3 and rhTpo. After 20 hours cells were stained for SKL and Hoechst-33342 and Pyronin-Y. The proportion of SKL cells in cell cycle were measured by FACS. Referring now to FIG. 12, representative flow plot showing cell cycle distribution of gated SKL cells and combined data for fold increase in cell cycle for dmPGE$_2$-treated cells compared to vehicle control from 3 experiments, Mean±SEM, n=9 mice, each assayed individually. The proportion of SKL cells in cell cycle were measured by FACS. Representative flow plot showing cell cycle distribution of gated SKL cells and combined data for fold increase in cell cycle for dmPGE$_2$-treated cells compared to vehicle control from 3 experiments, Mean±SEM, n=9 mice, each assayed individually.

13. PGE$_2$ Increases the Cell Cycle Rate of Highly Purified CD150$^+$48' (SLAM) SKL Cells In Vitro.

Referring now to FIG. 8, table summarizing data collected using Lin$^{neg}$ bone marrow cells treated with either 1 microMolar dmPGE$_2$ or vehicle for 2 hours and cultured in the presence of growth factors (50 ng/ml rmSCF, 100 ng/ml each of rhFlt-3 and rhTPO) for 20 hours, were stained for SLAM SKL, Hoechst-33342 and Pyronin-Y and the proportion of SLAM SKL cells in $G_o$, $G_1$, S and $G_2$/M phase of the cell cycle determined by quantitation of the DNA and the RNA content by FACS. Data are Mean±SEM for n=9 mice, each assayed individually. $^{(b)}$Percentage of cells in $G_1$+S+$G_2$M; Combined data for n=9 mice. $^{(*)}P<0.05$ compared to vehicle control.

14. Pulse Exposure to PGE$_2$ Increases Proliferation and Cell Cycle Rate of Homed SKL Cells In Vivo.

CD45.1 Lineage$^{neg}$ bone marrow cells were treated with dmPGE$_2$ or vehicle and transplanted into lethally irradiated CD45.2 mice. Immediately after transplantation, BrdU was provided in drinking water and administered by IP injection. Bone marrow was analyzed 16 hours later and the proportion of CD45.1$^+$, SKL cells that were BrdU$^+$ was analyzed by FACS analysis. Referring now to FIG. 13, CD45.1 Lin$^{neg}$ bone marrow cells were treated with dmPGE$_2$ or vehicle and transplanted into lethally irradiated CD45.2 mice. Immediately after transplantation, BrdU was provided in drinking water and administered by IP injection. Bone marrow was analyzed 16 hours later and the proportion of CD45.1$^+$, SKL cells that were BrdU$^+$ was analyzed by FACS analysis. A higher proportion of SKL cells treated with PGE$_2$ homed to marrow. Data are Mean±SEM, n=5 per mice/group, each assayed individually.

15. Long-Term Repopulating Activity of Stem Cells is Maintained after PGE$_2$ Pulse Exposure.

For head-to-head competitive analysis, WBM from CD45.1 and CD45.2 mice were treated with vehicle or dmPGE$_2$ and mixed with 2×10$^5$ competitor marrow cells from CD45.1/CD45.2 mice at various ratios and transplanted into lethally-irradiated CD45.1/CD45.2 mice. The proportion of CD45.1, CD45.2, and CD45.1/CD45.2 cells in PB was determined monthly. For secondary, tertiary and quaternary transplants, $2\times10^6$ WBM from previously transplanted CD45.1/CD45.2 mice at a 1:1 ratio were injected into lethally-irradiated CD45.1/CD45.2 mice in noncompetitive fashion. The proportion of CD45.1, CD45.2, and CD45.1/CD45.2 cells in PB was determined monthly. Referring now to FIG. 14, Increased chimerism of $dmPGE_2$-treated cells vs. vehicle is shown for primary transplant at 20 weeks (time of secondary transplant) and in a sub-cohort at 32 weeks (time of 12 week analysis of secondary transplant), for secondary transplant at 12 weeks and 24 weeks, and likewise for tertiary and quaternary transplants, each art 12 weeks. Data for 20 week primary transplant were from 2 pooled experiments, n=5 mice/group/experiment, each assayed individually. Data for secondary, tertiary, and quaternary transplants were from n=5 mice/group, each assayed individually 16. Peripheral Blood Stem Cell (PBSC) Mobilization Regimens for Indomethacin and G-CSF.

Mice were given SC treatments of 150 microgram/kg indomethacin or 150 microgram/kg baicalein (lipoxygenase inhibitor) in gelatin every 48 hours with or without G-CSF for 4 days. CFU-GM mobilization was determined as previously described (Pelus et. al., Experimental Hematology 33 (2005) 295-307). Referring now to FIGS. 7A & 7B, the combination of the dual cyclooxygenase inhibitor Indomethacin and G-CSF synergistically mobilize mouse HSPC. Effects of daily SC administration of 150 μm/kg indomethacin or 150 ug/kg baicalein (lipoxygenase inhibitor) alone (FIG. 7A) or with G-CSF (FIG. 7B) for 4 days on CFU-GM mobilization. Data are expressed as mean±SEM CFU-GM mobilized per ml of blood for N=3 mice each assayed.

Referring now to FIG. 16, mice were given daily, bid SC injections with G-CSF (1 microgram per mouse) or G-CSF+ indomethacin (50 microgram per mouse) for 4 days. CFU-GM mobilization was determined as described (Pelus et. al., Experimental Hematology 33 (2005) 295-307). Mice treated with the combination demonstrated a larger fold increase in CFU-GM per unit of blood than animals treated with only G-CSF.

Low density mononuclear cells from the peripheral blood of mice mobilized by the above regimen were analyzed for HSPC by FACS analysis. For detection of SKL and SLAM-SKL cells were stained with Sca-1-PE-Cy7, c-kit-APC, CD150-PECy5, CD48-FITC, Lineage Cocktail-Biotin, and secondary staining with Streptavidin-APC-Cy7. Referring now to FIG. 17, analyses were performed on a BD-LSR II. Flow cytometric analysis of phenotypically defined HSPC in peripheral blood of mice treated with G-CSF or the combination of G-CSF and Indomethacin. N=5 mice per group, each assayed individually.

17. Combination Mobilization by Indomethacin Plus AMD3100 Mobilizes HSPC.

Mice were given daily, bid SC injections with vehicle or Indomethacin (50 microgram per mouse) for four days. On day 5, mice were given either vehicle or AMD3100 (5 mg/kg). One hour later mice were sacrificed and CFU-GM mobilization was determined as previously described (Pelus et. al, Experimental Hematology 33 (2005) 295-307). Referring now to FIG. 18, Mobilization of CFU-GM by vehicle or Indomethacin treatment alone (left panel). Mobilization of CFU-GM by single administration of AMD3100, or Indomethacin treatment+AMD3100 (right panel). Data are expressed as mean±SEM, n=5 mice per group, each assayed individually.

18. Comparison of Mobilization Efficiency Employing Indomethacin in Combination with Various Mobilization Regimens.

Mice were treated with vehicle, indomethacin (50 microgram per mouse, bid SC, 4 days), AMD3100 (5 mg/kg day 5), G-CSF (1 microgram per mouse, bid SC, 4 days), AMD3100+GROβ (5 milligram/kg and 20 milligram/kg respectively, day 5), AMD3100+Indomethacin (Indomethacin 50 microgram per mouse, bid SC, 4 days; AMD3100 5 milligram/kg day 5), or G-CSF+Indomethacin (1 microgram and 50 microgram respectively, bid C, 4 days). CFU-GM mobilization was determined as previously described (Pelus et. al., Experimental Hematology 33 (2005) 295-307). Referring now to FIG. 19, CFU-GM per niL of peripheral blood plotted for various treatment regimes as outline in the above.

Mice were treated with vehicle, G-CSF (1 microgram per mouse, bid SC, 4 days), G-CSF+Indomethacin (50 microgram per mouse, bid SC, 4 days) or G-CSF+Meloxicam (0.3 mg/kg, bid SC, 4 days). CFU-GM mobilization was determined as previously described (Pelus et. al., Experimental Hematology 33 (2005) 295-307). Referring now to FIG. 20, a bar graph illustrating a comparison of mobilization induced by Indomethacin+G-CSF and the similar acting NSAID Meloxicam+G-CSF. Data are expressed as mean±SEM, n=5 mice per group, each assayed individually.

19. Staggered Dosing with NSAID Allows for Recovery of CXCR4 Expression on HSPC.

CD45.1 mice were mobilized with G-CSF (1 microgram per mouse, bid, SC, 4 days) or G-CSF+Indomethacin (50 microgram per mouse, bid, SC, 4 days) and peripheral blood mononuclear cells (PBMC) were collected at day 5. PBMC were mixed at various ratios with CD45.2 bone marrow and transplanted into lethally irradiated (1100 cGy, split dose) CD45.2 mice. Referring now to FIG. 21, competitive repopulating units are shown at 12 weeks post transplant (left panel). Data are expressed as mean±SEM from 2 experiments, N=5 mice per group, per experiment, each assayed individually. Since there was no improvement in engraftment with PBMC mobilized by indomethacin co-administered with G-CSF compared to G-CSF alone, it was hypothesized that deficits in homing may occur as a result of a decrease in CXCR4 receptor expression, and that this could be alleviated by staggering the indomethacin and G-CSF treatments. CD45.2 mice were mobilized with G-CSF (1 microgram per mouse, bid, SC, 4 days), G-CSF+ Indomethacin without a stagger (50 microgram per mouse, bid, SC, 4 days), G-CSF+Indomethacin with a 1 day stagger (Indomethacin started first and given for 4 days, and G-CSF given for 4 days starting on the second indomethacin treatment, creating 1 day with G-CSF without indomethacin before collection of PBMC), or G-CSF+Indomethacin with a 2 day stagger (Indomethacin started first and given for 4 days, and G-CSF given for 4 days starting on the third indomethacin treatment, creating 2 days with G-CSF without Indomethacin before collection of PBMC). Referring now to FIG. 21 (right panel) the expression of CXCR4 on SKL cells is shown. Data are expressed as mean±SEM, N=5 mice per group, each assayed individually.

20. Mobilized PBSC from G-CSF Plus NSAID Treated Mice Show Significantly Enhanced Long-Term Stem Cell Function Compared to PBSC Mobilized by G-CSF Alone.

CD45.1 mice were mobilized with G-CSF or G-CSF+ Indomethacin (1 day stagger) and PBMC were transplanted with CD45.2 competitor bone marrow into lethally irradiated CD45.2 mice. Referring now to FIG. 22, chimerism at multiple donor: competitor ratios (left panel) and competitive repopulating units (right panel) are shown at 12 weeks post-transplant. Data are expressed as mean±SEM, n=5 mice per group, each assayed individually.

21. PBSC from G-CSF Plus NSAID Mobilized Mice Restore Peripheral Blood Neutrophil Counts Faster when Transplanted into Lethally Irradiated Mice Compared to PBSC Mobilized by G-CSF Alone.

Mice were mobilized with G-CSF or G-CSF+Meloxicam (1 day stagger) and $2 \times 10^6$ PBMC were transplanted into lethally irradiated recipients. Neutrophils in blood were enumerated every other day by a Hemavet 950 FS (Drew Scientific) until full recovery (compared to control subset). Platelets in blood were enumerated every other day by a Hemavet 950 FS (Drew Scientific) until full recovery (compared to control subset). Referring now to FIG. 23, Neutrophils in peripheral blood (PB) were enumerated every other day until full recovery (compared to control subset). These data are expressed as mean±SEM, n-10 mice per group, each assayed individually. Referring now to FIG. 24, platelets in peripheral blood (PB) were enumerated every other day until full recovery (compared to control subset). The data are expressed as mean±SEM, n=10 mice per group, each assayed individually.

22. Determining the Effect of G-CSF and Meloxicam on Cell Mobilization in Baboons.

Referring now to FIG. 25, a first group of baboons was mobilized with the following dosing regime treatment with 10 ug/kg of body weight of G-CSF then after a two week wash out period the animals were treated with 10 ug/kg G-CSF plus 0.1 mg/kg of meloxicam. A second group of baboon was mobilized with the following regime 10 ug/kg G-CSF plus 0.1 mg/kg of meloxicam and after a two week wash out period with 10 ug/kg G-CSF. Referring now to FIG. 26, $CD34^+$ cells in PB were determined by FACS analysis and CFU-GM per ml of blood determined as previously described. Co-administering G-CSF and Meloxicam increased mobilization of $CD34^+$ cells (left panel) and CFU-GM measured per unit of blood drawn.

23. Optimal Enhancement of PBSC Mobilization in Mice Requires Inhibition of Both COX1 and COX 2 Enzymes.

Mice were mobilized with G-CSF and CFU-GM in PB was compared to mobilization regimens with G-CSF and the combination of various NSAIDS (Aspirin [COX-1 and COX-2]; Licofelone [COX-2 and 5-LOX]; SC-560 [COX-1]; Valeryl Salicylate [COX-1]; Valdecoxib [COX-2]; NS-398 [COX-2]). Referring now to FIG. 27, the results of these tests are summarized and these data are expressed as mean±SEM, n=4 mice per group, each assayed individually. Compounds that are known to inhibit both COX1 and 2 were better at mobilizing colony forming cells than compounds that are considered highly selective for only one of the two isozymes, in order to test the efficacy of two commonly used COX inhibitors, mice were mobilized with G-CSF or the combination of G-CSF and aspirin or ibuprofen (PO., bid, 4 days). CFU-GM was determined as previously described. Referring now to FIG. 28, dose-response analysis of G-CSF+Aspirin and G-CSF+Ibuprofen mobilization of CFU-GM to peripheral blood are present in bar graph form for a control group of mice treated with only G-CSF; for mice treated with G-CSF plus 10, 20 or 40 milligram/kg of aspirin; and for mice treated with G-CSF plus 10, 20 or 40 milligram/kg of ibuprofen. Data are expressed as mean±SEM, n=4 mice per group, each assayed individually.

24. Measuring the Dose Dependent Effect of Meloxicam on CFU in Mice

Mice were mobilized with G-CSF and following doses of meloxicam 0.0 (control) 0.02, 0.2, 0.5, 1.5, and 3 milligram/kg of body weight for meloxicam (bid SC, 4 days) and CFU-GM was determined as previously described. Referring now to FIG. 29 the dose response of meloxicam on HSPC was measured in samples of the animals' peripheral blood; or in the animals' bone marrow (FIG. 30). These data are expressed as mean±SEM, n=3 mice per group, each assayed individually.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES

Breyer, R. M, Bagdassarian, C. K., Myers, S. A., and Breyer, M. D. (2001). Prostanoid receptors: subtypes and signaling. Annu. Rev. Pharmacol. Toxicol. 41, 661-690.

Broxmeyer, H. E. (2006). Cord Blood Hematopoietic Stem and Progenitor Cells. In Essentials of Stem Cell Biology, Elsevier, Inc.), pp. 133-137.

Cheng, T., Rodrigues, N., Shen, H., Yang, Y., Dombkowski, D., Sykes, M, and Scadden, D. T. (2000). Hematopoietic stem cell quiescence maintained by p21cip1/waf1. Science 287, 1804-1808.

Fleming, H. E., Janzen, V., Lo, C. C, Guo, J., Leahy, K. M., Kronenberg, H. M., and Scadden, D. T. (2008). Wnt signaling in the niche enforces hematopoietic stem cell quiescence and is necessary to preserve self-renewal in vivo. Cell Stem Cell 2, 274-283.

Fruehauf, S. and Seggewiss, R. (2003). It's moving day: factors affecting peripheral blood stem cell mobilization and strategies for improvement [corrected]. Br. J. Haematol. 122, 360-375.

Fukuda, S., Mantel, C. R., and Pelus, L. M. (2004). Survivin regulates hematopoietic progenitor cell proliferation through p21 WAF 1/Cip1-dependent and -independent pathways. Blood 103, 120-127.

Fukuda, S. and Pelus, L. M. (2001). Regulation of the inhibitor-of-apoptosis family member survivin in normal cord blood and bone marrow CD34(+) cells by hematopoietic growth factors: implication of survivin expression in normal hematopoiesis. Blood 98, 2091-2100.

Goldman, J. M. and Horowitz, M. M. (2002). The international bone marrow transplant registry. Int. J. Hematol. 76 Suppl 1, 393-397.

Hall, K. M., Horvath, T. L, Abonour, R., Cornetta, K., and Srour, E. F. (2006). Decreased homing of retro virally transduced human bone marrow CD34+ cells in the NOD/SCID mouse model. Exp. Hematol. 34, 433-442.

Janzen, V., Fleming, H. E., Riedt, T., Karlsson, G., Riese, M J., Lo, C. C, Reynolds, G., Milne, C. D., Paige, C. J., Karlsson, S., Woo, M., and Scadden, D. T. (2008). Hematopoietic stem cell responsiveness to exogenous signals is limited by caspase-3. Cell Stem Cell 2, 584-594.

Khan, N. I. and Bendall, L, J. (2006). Role of WNT signaling in normal and malignant hematopoiesis. Histol. Histopathol. 21, 761-774.

Li, F., Ambrosini, G., Chu, E. Y., Plescia, J., Tognin, S., Marchisio, P. C, and Altieri, D. C. (1998). Control of apoptosis and mitotic spindle checkpoint by survivin. Nature 396, 580-584.

Liu, X. H., Kirschenbaum, A., Lu, M., Yao, S., Dosoretz, A., Holland J. F., and Levine, A. C. (2002). Prostaglandin E2 induces hypoxia-inducible factor-1 alpha stabilization and nuclear localization in a human prostate cancer cell line. J Biol Chem 277, 50081-50086.

Muller-Sieburg, C. E. and Sieburg, H. B. (2006). Clonal diversity of the stem cell compartment. Curr Opin Hematol 13, 243-248.

Namba, T., Sugimoto, Y., Negishi, M., Irie, A-, Ushikubi, F., Kakizuka, A-, Ito, S., Ichikawa, A., and Narumiya, S. (1993). Alternative splicing of C-terminal tail of prostaglandin E receptor subtype EP3 determines G-protein specificity. Nature 365, 166-170.

North, T. E., Goessling, W., Walkley, C. R., Lengerke, C, Kopani. K. R., Lord, A-M., Weber, G. J., Bowman, T. V., Jang J. H., Grosser, T., Fitzgerald, G. A., Daley, G. Q., Orkin, S. H., and Zon, L, I. (2007). Prostaglandin E2 regulates vertebrate haematopoietic stem cell homeostasis. Nature 447, 1007-1011.

Okada, S., Nakauchi, H., Nagayoshi, K., Nishikawa, S., Miura, Y., and Suda. T. (1992). In vivo and in vitro stem cell function of c-kit- and Sea-1-positive murine hematopoietic cells. Blood 80, 3044-3050.

Peng, X. H., Karna, P., Cao, Z., Jiang, B. H., Zhou, M., and Yang, L. (2006). Cross-talk between epidermal growth factor receptor and hypoxia-inducible factor-1 alpha signal pathways increases resistance to apoptosis by up-regulating survivin gene expression. J Biol Chem 281, 25903-25914.

Piccoli, C, D'Aprile, A., Ripoli, M., Scrima, R., Boffoli, D., Tabilio, A., and Capitanio, N. (2007). The hypoxia-inducible factor is stabilized in circulating hematopoietic stem cells under normoxic conditions. FEBS Lett 581, 3111-3119.

Porecha, N. K., English, K., Hangoc, G., Broxmeyer, H. E., and Christopherson, K. W. (2006). Enhanced functional response to CXCL1 2/SDF-1 through retroviral overexpression of CXCR4 on M07e cells: implications for hematopoietic stem cell transplantation. Stem Cells Dev. 75, 325-333.

Pulsipher M A, Chitphakdithai P, Logan B R, Leitman S F, Anderlini P, Klein J P, Horowitz M M, Miller J P, King R J, Confer D L, Donor, recipient, and transplant characteristics as risk factors after unrelated donor PBSC transplantation: beneficial effects of higher CD34+ cell dose. Blood. 2009 Sep. 24;114(13):2606-16. Epub 2009 Jul. 16.

Regan, J. W. (2003). EP2 and EP4 prostanoid receptor signaling. Life Sci. 74, 143-153.

Spangrude, G J. and Scollay, R. (1990). A simplified method for enrichment of mouse hematopoietic stem cells. Exp. Hematol. 75, 920-926.

Staller, P., Sulitkova, J., Lisztwan, J., Moch, H., Oakeley, E. J., and Krek, W. (2003). Chemokine receptor CXCR4 downregulated by von Hippel-Lindau tumour suppressor pVHL. Nature 425, 307-311.

Sugimoto, Y. and Narumiya, S. (2007). Prostaglandin E receptors. J. Biol. Chem. 282, 11613-11617.

Tamm, L, Wang, Y., Sausville, E., Scudiero, D. A., Vigna, N., Oltersdorf, T., and Reed, J. C. (1998). IAP-family protein survivin inhibits caspase activity and apoptosis induced by Fas (CD95), Bax, caspases, and anticancer drugs. Cancer Res. 58, 5315-5320.

Tsuboi,K., SugimotOjY., and Ichikawa, A. (2002). Prostanoid receptor subtypes. Prostaglandins Other Lipid Mediat. 68-69, 535-556.

Zagzag, D., Krishnamachary, B., Yee, H., Okuyama, H., Chiriboga, L., Ali, M. A., Melamed J., and Semenza, G. L. (2005). Stromal cell-derived factor-1 alpha and CXCR4 expression in hemangioblastoma and clear cell-renal cell carcinoma: von Hippel-Lindau loss-of-function induces expression of a ligand and its receptor. Cancer Res 65, 6178-6188.

We claim:

1. A composition for use in an ex vivo method of enhancing viral transduction efficacy, the composition comprising:
   (a) an isolated population of mononuclear cells consisting essentially of CD34$^+$ human hematopoietic stem or progenitor cells;
   (b) a prostaglandin $E_2$ or a derivative thereof in an amount sufficient to enhance ex vivo viral transduction efficacy of the isolated population of mononuclear cells; and
   (c) a viral vector that contains at least one gene of interest.

2. The composition of claim 1, wherein the prostaglandin $E_2$ or a derivative thereof is selected from the group consisting of $PGE_2$ and $dmPGE_2$.

3. The composition of claim 1, wherein the prostaglandin $E_2$ or a derivative thereof is present at a concentration of about 1 μM to about 10 μM.

4. The composition of claim 1, wherein the prostaglandin $E_2$ or a derivative thereof is present at a concentration of about 1 μM.

5. A cell transplant for gene therapy consisting essentially of CD34$^+$ hematopoietic stem and/or progenitor cells, wherein the CD34$^+$ hematopoietic stem and/or progenitor cells have been ex vivo:
   (a) contacted with an amount of a prostaglandin $E_2$ or a derivative thereof sufficient to enhance viral transduction efficacy of the cells; and
   (b) transduced with a viral vector that contains at least one gene of interest; wherein the cells are contacted with the viral vector within 24 hours of exposure to the prostaglandin $E_2$ or derivative thereof in the absence of non-CD34$^+$ cells,
   wherein the CD34$^+$ hematopoietic stem and/or progenitor cells have reduced apoptosis compared to a non-contacted hematopoietic stem and/or progenitor cell.

6. The cell transplant according to claim 5, wherein the cells are contacted with the prostaglandin $E_2$ or a derivative thereof for at least one hour.

7. The cell transplant according to claim 5, wherein the cells are contacted with the prostaglandin $E_2$ or a derivative thereof for at about one hour to about 6 hours.

8. The cell transplant according to claim 5, wherein the prostaglandin $E_2$ or a derivative thereof is selected from the group consisting of $PGE_2$ and $dmPGE_2$.

9. The cell transplant according to claim 5, wherein the hematopoietic stem and/or progenitor cells are Lineage negative (Lin$^{Neg}$) cells.

10. The cell transplant according to claim 5, wherein the hematopoietic stem and/or progenitor cells are human hematopoietic stem cells.

11. The cell transplant according to claim 5, wherein the hematopoietic stem and/or progenitor cells have increased Survivin expression by about 2.4 fold compared to the expression in a non-contacted hematopoietic stem and/or progenitor cell.

\* \* \* \* \*

UNITED STATES PATENT AND TRADEMARK OFFICE
CERTIFICATE OF CORRECTION

PATENT NO. : 11,241,454 B2  
APPLICATION NO. : 15/592375  
DATED : February 8, 2022  
INVENTOR(S) : Louis M. Pelus et al.

Page 1 of 1

It is certified that error appears in the above-identified patent and that said Letters Patent is hereby corrected as shown below:

In the Specification

Column 5, Line 5, "$Lin^{neg}$ marrow" should be --$Lin^{neg}$ bone marrow--.

Column 17, Line 44, "SDF-1a" should be --SDF-1α--.

Column 17, Line 50, "SDf-1a" should be --SDF-1α--.

Signed and Sealed this  
Eighth Day of November, 2022

Katherine Kelly Vidal  
*Director of the United States Patent and Trademark Office*